United States Patent [19]

Temple, Jr.

[11] 4,234,581

[45] Nov. 18, 1980

[54] THIENO[2,3-D]OXAZINES

[75] Inventor: Davis L. Temple, Jr., Evansville, Ind.

[73] Assignee: Mead Johnson & Company, Evansville, Ind.

[21] Appl. No.: 25,295

[22] Filed: Mar. 30, 1979

Related U.S. Application Data

[60] Division of Ser. No. 826,591, Sep. 10, 1975, Pat. No. 4,159,377, which is a continuation-in-part of Ser. No. 611,955, Sep. 10, 1975, Pat. No. 4,054,656.

[51] Int. Cl.$^3$ .................... A61K 31/38; C07D 498/04
[52] U.S. Cl. .................... 424/248.51; 544/91
[58] Field of Search .................... 544/91, 89; 549/69; 424/275, 248.51

[56] References Cited

U.S. PATENT DOCUMENTS

| | | | |
|---|---|---|---|
| 3,953,468 | 4/1976 | Wechter et al. | 424/275 X |
| 3,966,965 | 6/1976 | Sellstedt et al. | 424/309 |
| 4,054,656 | 10/1977 | Temple, Jr. | 424/251 |
| 4,159,377 | 6/1979 | Temple, Jr. | 544/278 |

OTHER PUBLICATIONS

Fitton et al., J. Chem. Soc. (6), 1971, pp. 146 to 149.

Shvedov et al., Chem. Abstracts, vol. 66, abst. 37,711w (1967).
Nakanishi et al., Chem. Abst. vol. 78, abst. 29795j (1973) (abst. of Jap. Pat. 73–42,271).
Lorente et al., Chem. Abst. vol. 83, abst. 178980w (1975).
Temple et al., J. Med. Chem., vol. 22, No. 5, pp. 505 to 510, (1979).

*Primary Examiner*—John D. Randolph
*Attorney, Agent, or Firm*—Robert E. Carnahan; Robert H. Uloth

[57] ABSTRACT

2-Aminothiophene-3-carboxamides are converted to oxamates or fumaramides by acylation of the amino group. Cyclization yields thieno[2,3-d]pyrimidines which may also be prepared from the corresponding oxazines. Compounds illustrative of those having inhibitory action on the immediate hypersensitivity reaction in mammals are N-[3-(aminocarbonyl)-4,5,6,7-tetrahydrobenzo[b]thien-2-yl]oxamic acid, ethyl 5,6,7,8-tetrahydro-4-oxo-4$\underline{H}$-benzothieno[2,3-d][1,3]oxazine-2-carboxylate, and ethyl 3,4-dihydro-6-ethyl-4-oxothieno[2,3-d]pyrimidine-2-carboxylate.

26 Claims, No Drawings

THIENO[2,3-D]OXAZINES

CROSS REFERENCE TO RELATED APPLICATION

This application is a division of application Ser. No. 826,591 Sept. 10, 1975, now U.S. Pat. No. 4,159,377 patented June 26, 1979 which is a continuation-in-part of application Ser. No. 611,955 filed Sept. 10, 1975 and now U.S. Pat. No. 4,054,656 patented Oct. 18, 1977. The disclosure herein is identical with that of Ser. No. 611,955 except for that following Procedure 82.

FIELD OF THE INVENTION

This invention involves a novel series of pyrimidine compounds having a fused thiophene ring, namely a series of thieno[2,3-d]pyrimidines, and the structurally related thieno-oxazines, and thienylamides which are intermediates in the synthesis of the pyrimidines. It also relates to therapeutic methods and compositions employing one of the thieno[2,3-d]pyrimidines, thieno-oxazines, or thienyloxamates as the active ingredient.

DESCRIPTION OF THE PRIOR ART

The literature most closely related to the subject of this invention is represented by the following references.

1. West German patent application No. 2,104,435 published Aug. 26, 1971, "New Benzothienopyrimidine Derivatives, Procedure for Their Preparation and Their Application in Pharmaceutics."
2. Sauter, et al., Monatsh. 105, 558–562 (1974), "Synthesis of Basically Substituted [1]Benzothieno[2,3-d]pyrimidine Derivatives ... "
3. Sauter, et al., Monatsh. 105, 1258–1265 (1974), "Cyclization Reactions to Thiazolo[2,3-a]thieno[2,3-d]pyrimidines."
4. Robba, et al., Bull. Soc. Chim. France, (1974) 2864–2870, "No. 562.- Thienopyrimidines. IV.- Synthesis and Study of Derivatives of Thiophene Amino Acids and Aminoketones."
5. Wright, et al., J. Med. Chem. 16, 861–2 (1973), "Antiasthma Agents. 1. 4-Oxo-4H-[1]benzothieno[2,3-b]pyran-2-carboxylic Acid and 4-Oxo-4H-[1]benzofuro[3,2-b]pyran-2-carboxylic Acid."
6. Hall, et al., J. Med. Chem. 17, 685–690 (1974), "Quinoline Derivatives as Antiallergy Agents."
7. Barth, U.S. Pat. No. 3,883,653 (May 13, 1975). Method of Preventing Asthmatic Symptoms.
8. Sellstedt, et al., U.S. Pat. No. 3,888,858 (June 10, 1975). 3,4-Dihydro-4-oxo-2-quinazolinecarboxyic Acids, Salts and Esters as Anti-allergic Agents.
9. Narr, et al., U.S. Pat. No. 3,888,851 (June 10, 1975). 2,4-Diamino-Substituted Thieno[3,2-b]pyrimidines and Salts Thereof.
10. Baetz, U.S. Pat. No. 3,888,983 (June 10, 1975). Derivatives of Thazolino-pyrimidin-6-ones, In Inducing Analgesia.
11. McClelland, et al., J. Chem. Soc. 78–81 (1948). "Some 1:3-Oxazine Derivatives of Thionaphthen."
12. Tinney, et al., J. Med. Chem. 17, 624–630 (1974). "Synthesis and Pharmacological Evaluation of 2,3-Dihydro-1H-thieno[2,3-e][1,4]diazepines.

References 1, 2, and 3 refer to various thieno[2,3-d]pyrimidines, but these substances are distinguished by the nature of the substituents in the 2-position and the lack of disclosure of anti-allergic utility.

Reference 4 refers to 2-aminothiophene-3-carboxylates and -carboxamides useful for preparing thieno[2,3-d]pyrimidines.

References 5, 6, 7, and 8 involve heterocyclic organic compounds having anti-allergic activity of the type with which the present invention is concerned but these substances involve different heterocyclic ring systems than the thieno[2,3-d]pyrimidines of the present invention.

References 9, 10, and 11 involve pyrimidine compounds having a thiophene ring fused thereto, but they too represent different heterocyclic systems from those with which the present invention is concerned, and different medical utilities.

Reference 12 refers to hexahydrobenzothieno[2,3-e][1,4]diazepin-2-ones which were synthesized for evaluation as anti-anxiety agents.

SUMMARY OF THE INVENTION

This invention provides compounds of Formulas I, IV and V

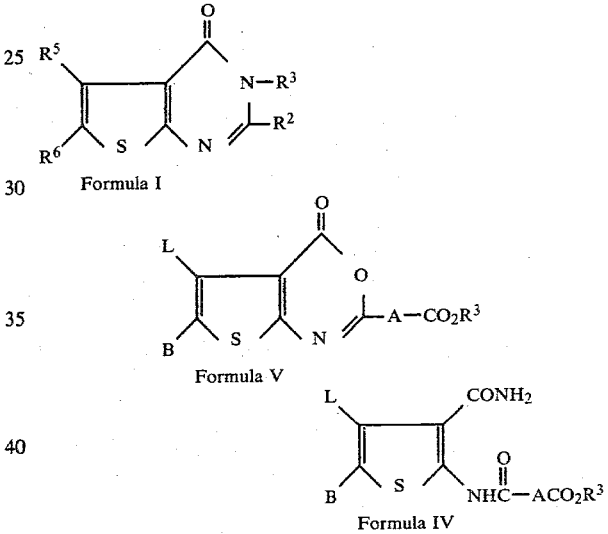

Formula I

Formula V

Formula IV

These substances are useful in the treatment of diseases of allergy and particularly asthma, hay fever, and food allergy which are characterized by episodes of acute attack provoked by inhalation or ingestion of an allergen. The compounds have the advantage for chronic prophylactic use of being substantially free of other pharmacologic activity, and they have low toxicities. Preferred members are orally active.

The compounds of Formulas IV and V are also useful as intermediates for the manufacture of the compounds of Formula I.

In Formula I, the symbol $R^2$ refers to a carboxylic acid substituent or a lower alkyl ester or nontoxic pharmacologically inert metal salt thereof. It also refers to the vinylogous carboxylic acids, esters, and salts in which $R^2$ is the substituent of $CH=CHCO_2R^3$ and which $R^3$ is hydrogen, lower alkyl having 1–8 carbon atoms, or a nontoxic pharmacologically inert metal cation. By nontoxic pharmacologically inert is meant that the cation in the doses required for the administration of one of the salts containing it is without deleterious effect or interfering pharmacologically action on the host. Suitable metal cations are preferably the alkali metals sodium and potassium, but also other nontoxic pharmacologically inert cations such as calcium, magnesium, aluminum, zinc, and barium. $R^2$ may also be the methylol group or the formate, or a lower alkyl ester thereof. $R^2$ may also be the carboxaldehyde, 5-tetrazolyl, or N-(tetrazol-5-yl)carbamyl group. To sum up, $R^2$ is a group having one of the following formulas in which $R^3$ has the meaning given above, and R is lower alkyl having 1 to 8 carbon atoms.

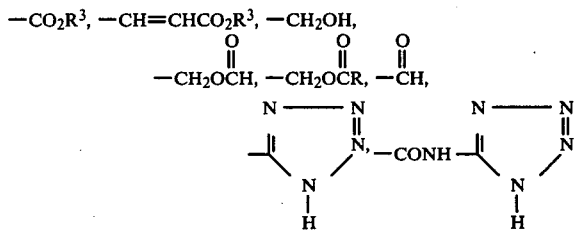

In Formula I, $R^3$ is the same as above, and $R^5$ and $R^6$ may be hydrogen, lower alkyl having from 1 to 8 carbon atoms, lower alkenyl having from 3 to 6 carbon atoms, lower alkoxy having from 1 to 6 carbon atoms, hydroxy, nitro, amino, halo including chlorine, bromine, iodine, and fluorine, phenyl, alkanoyl having from 2 to 6 carbon atoms or they are bonded to one another to form a cycloalkene ring fused to the thiophene ring and having a total of from 5 to 7 annular ring carbon atoms or an R-substituted cycloalkene having 5 to 7 annular ring carbon atoms wherein R has the same meaning as above.

In Formula V, $R^3$ has the same meaning as above and A is either a covalent bond linking the —$CO_2R^3$ group to the ring or it is the vinyl group, —CH=CH—, joining the —$CO_2R^3$ group to the ring. The symbols L and B signify some of the same groups identified for $R^5$ and $R^6$, but their definition is somewhat more limited. L and B may be hydrogen, lower alkyl having from 1 to 8 carbon atoms, lower alkenyl having from 3 to 6 carbon atoms, phenyl, alkanoyl having from 2 to 6 carbon atoms, or they may be joined to form a cycloalkene ring fused to the thiophene ring and having from 5 to 7 annular ring carbon atoms or R-substituted cycloalkene having from 5 to 7 annular ring carbon atoms wherein R has the same meaning as above.

In Formula IV, the symbols $R^3$, A, L and B have the same meaning as is indicated for Formula V.

DETAILED DESCRIPTION OF THE INVENTION

The compounds of Formulas I, IV and V inhibit the degranulation of sensitized mast cells. Immediate hypersensitivity reactions such as asthma, hay fever, allergic rhinitis, urticaria, and food allergy are believed to be mediated by reaction of immunoglobulin E, sometimes referred to as reaginic antibody with an antigen on the cell membrane of a mast cell to initiate reactions within the mast cell which ultimately release mediators such as bradykinin, histamine, serotonin, or slow reacting substance-A (SRS-A). The mediators effect changes in end organs such as airways, blood vessel, skin, and mucus membranes resulting in the symptoms of an allergic attack. The present substances are believed to prevent the release of mediators thereby preventing the allergic attack. They are, therefore, useful in the prophylactic treatment of subjects possessing hypersensitivities of the foregoing types, and inhibit acute allergic attacks such as an asthmatic attack. Preferred compounds are distinguished particulary by the fact that they are orally active, have very low toxicities, and are substantially devoid of other types of pharmacologic action including antihistaminic action. Thus, they are not primarily of value in the treatment of the fulminating allergic reactions but are of particular value for use prophylactically by hypersensitive subjects to prevent the manifestations of allergic reaction on exposure to an allergen for the hypersensitive condition.

Activity of test compounds in the passive cutaneous anaphylaxis reaction (PCA) in the rat has been shown in the prior art to correlate with the utility of active compounds in the treatment of immediate hypersensitivity conditions such as asthma. Rat reaginic antiserum is prepared substantially according to the method of Mota, Immunology 7, 681–699 (1964) employing male Sprague-Dawley (Carworth Farms) or Wistar (Harlan) rats weighing 100–175 g. which are injected intramuscularly with a solution of egg albumin in saline at a dose of 10 mg. per kg. and intraperitoneally with $2 \times 10^{10}$ Bordetella pertussis organisms. Twelve days after injection, the serum is collected and the antibody titer is determined. The sera are pooled which contain sufficient antibody to cause a 10 mm. spot in the dorsal skin of the rat in the PCA test after dilution 10 fold. The highest dilution of antiserum capable of inducing PCA in the rat 48 to 72 hrs. after injection is normally in the range of 50–80. The selected reaginic anti-sera are stored frozen until use.

For carrying out the test, groups of 5 to 10 male Sprague-Dawley (Carworth Farms) rats, each rat weighing 100–150 g., are used. Forty-eight hours prior to the test, the animals are passively sensitized by intradermal injection of 0.1 ml. of diluted antiserum at various locations on the shaved skin of the back. A dilution of antiserum is used so that a spot following challenge of 20–25 mm. in diameter is obtained. A higher dilution of the antiserum is injected in at least one location to allow a more sensitive measure of the activity of less potent compounds. A latent period of 48 hrs. is usually allowed before the animals are challenged. According to the usual screening procedure, 15 min. prior to challenge the test drug is administered either by intraperitoneal injection, intravenous injection, or orally by gavage. Challenge involves an intravenous injection of a dose of 25 mg./kg. of egg albumin and 25 mg./kg. of Evans' blue dye in saline. The dye serves simply as a marker. The response of the antigen challenge in the localities on the skin which have been previously sensitized results in increased capillary permeability at the sensitized site and leakage of the blue dye into the area surrounding the sensitized site. The PCA response is scored by measuring the mean spot diameter on the excised and reversed skin 20–30 min. after challange. In each experiment a group of control animals receiving no drug is employed. The percent inhibition of the PCA is calculated by determining the mean diameters of the spots in the control and treated animals and computing the difference between the squares of the mean diameters of the control animals and the treated animals and expressing this difference as a percentage of the square of the mean diameter of the control animals. Results are expressed as percent inhibition.

Rats may be injected intradermally with 0.1 ml. of a solution containing 1 mg./ml. histamine 10 min. prior to sacrificing. This permits a determination of whether the test compound is exerting an antihistaminic effect on the end organ rather than interfering with mediator release from the mast cells in inhibiting the PCA.

Various doses of test compound in parallel experiments are employed when a dose response curve is to be constructed for quantitative comparison of potencies among active compounds. The $ID_{50}$, the dose at which 50% inhibition of the PCA occurs, is determined by interpolation. In other modifications, various time intervals are allowed between drug treatment and challenge to ascertain the duration of drug effect.

A more sophisticated test reflecting the utility of the present substances in the treatment of immunologically induced bronchoconstriction involves an allergic respiratory model in the rat in which male Harlan rats weighing 225-275 g. each are actively sensitized with egg albumin and *B. pertussis* vaccine ($2 \times 10^{10}$ organisms per rat) as before for the preparation of the reaginic antisera. Thirteen to fifteen days after sensitization, the rats are prepared for intraduodenal administration of compounds by exposure of the duodenum through a small abdominal incision, and the jugular vein, carotid artery, and trachea are cannulated. The jugular vein cannula is used for the administration of the egg albumin challange and blood pressure is measured through the cannulated carotoid artery. The tracheal cannula is connected to a glass T-tube one arm of which is open to the atmosphere, and the other arm of which is connected to a pressure transducer for the measurement of the inspiratory and expiratory pressure. Changes in inspiratory and expiratory pressure are monitored as a reflection of changes in airway resistance following challange with the egg albumin antigen. The drugs are administered intraduodenally 15 min. prior to challenge with an injection of egg albumin and the changes in airway resistance relative to the control animals are determined. The antigenic challenge dose is adjusted to effect an approximately 36% decrease in inspiratory and expiratory pressure since this was found to be approximately the maximum which the animals can survive. The drug effect on this decrease in inspiratory and expiratory pressure is then determined for various doses of drug. That dose which produces the half maximal response is determined by interpolation from a dose response curve ($ID_{\frac{1}{2}}$ max.).

The data shown in the following table reflects the oral anti-allergic action some of the substances of the present invention in the foregoing tests.

| | Oral Anti-Allergic Action In Rats | | |
|---|---|---|---|
| Drug | PCA Response ($ID_{50}$, mg./kg.) | Allergic Respiratory Response ($ID_{178}$ max. mg./kg.) | $LD_{50}$ * (mg./kg.) |
| Procedure 2 | 15.4 | 3.8 | > 3160 |
| Procedure 27 | 11.4 | | |
| Procedure 28 | < 5.0 | | |
| Procedure 29 | 3.1 | 1.0 | 1600-5000** |
| Procedure 36 | 15.0 | | |
| Procedure 43 | 6.7 | | |
| Procedure 44 | 13.0 | | |
| Procedure 53 | 28.0+ | | |
| Procedure 55 | 34.0+ | | |
| Procedure 56 | 28.0 | | |

*Acute oral toxicity in the rat.
**$LD_{50}$ is greater than 1600 mg./kg., but less than 5000 mg./kg.
+2 hr. interval between drug dosage and challenge.

Cromolyn sodium is inactive on oral administration in the foregoing tests. This substance is used clinically in the prophylatic treatment of asthmatic patients by oral inhalation and its activity is reflected in the foregoing rat PCA test when it is administered by the intravenous or intraperitoneal injection. An $ID_{50}$ of approximately 1 mg./kg. can be demonstrated in the rat in the PCA test when cromolyn sodium is administered intravenously simultaneously with the antigen. Similarly, the intrinsic activity of these substances of the present invention which exhibit a reduced level of activity in the PCA test when administered by the oral route, as compared to the activity of the substances listed in the foregoing table, may be shown by administration thereof to the test animal by either the intraperitoneal or intravenous routes.

The activity of the present substances in interfering with the release of allergic mediator substances may be demonstrated in vitro by a test involving antagonism of antigen-induced histamine release from passively sensitized rat peritoneal mast cells. The method employed is similar to that described by Kusner, et al., Journal of Pharmacology and Experimental Therapeutics 184, 41-46 (1973). The test involves isolation of mast cells from the rat by lavage of the peritoneal cavity and isolation of the cellular material from the lavage fluid. The cells are sensitized by shaking in antiserum from rats sensitized as described above with respect to the passive cutaneous anaphylaxis test. The sensitized cells are then exposed to the egg albumin antigen and the release of histamine from the cells is measured by an automated fluorometric method. The inhibition of histamine release by the presence of a test compound during challenge of the sensitized cells is a measure of the activity of the test compound. Dose response curves are prepared employing various concentrations of the test substance and the concentration which inhibits histamine release by 50% ($IC_{50}$) is determined by interpolation. Cromolyn sodium was found to exhibit an $IC_{50}$ of 1 $\mu$m in this test system. The compounds of the present invention prepared by Procedures 2, 3, and 36 were substantially more potent than cromolyn sodium in that $IC_{50}$ values within the range of 0.3 to 0.8 $\mu$M were exhibited.

Thus, there is provided by the present invention a method for suppressing the allergic manifestations of immediate hypersensitivity in sensitive warm blooded animals on exposure thereof to the causative allergen. Mammals subject to immediate hypersensitivity sensitization include man, mouse, rat, hamster, gerbil, dog, cat, sheep, goat, horse, cow, etc. The process involves administering an effective dose of one of the compounds of the present invention by the oral, topical, parenteral, or inhalational routes. The effective dosage range in rats is from about 1 to 200 mg./kg. of body weight with the preferred compounds being effective orally in the range of from about 1 to 15 mg./kg. of body weight. The estimated human dose for the substance of Procedure 29 is in the range of from 1 to 500 mg. orally.

Appropriate dosage unit forms for the foregoing application of the substances of Formulas I, IV, and V such as tablets, solutions or suspensions for injection or inhalation, and powders for inhalation may be prepared with conventional pharmaceutical carriers according to established practices in the pharmaceutical art.

The compounds of the present invention are prepared from the 2-aminothiophene-3-carboxamides or 2-aminothiophene-3-carboxylic acids of Formula II shown in the following diagram wherein Z is —OH or —NH$_2$. Compounds of Formula II have been previously described by Gewald, et al., Chem. Berichte 98, 3571 (1965), and ibid., 99, 94 (1966). Novel compounds of Formula II for use in preparing compounds of this invention may be prepared by obvious adaptations of the Gewald, et al. methods. In Formula II the symbols L and B are independently selected from the group consisting of hydrogen, lower alkyl having 1 to 8 carbon atoms, lower alkenyl having 3 to 6 carbon atoms, phenyl, alkanoyl having 2 to 6 carbon atoms, or together they constitute cycloalkene having 5 to 7 annular ring carbon atoms or R-substituted cycloalkene having 5 to 7 annular ring carbon atoms wherein R is a lower alkyl group having 1 to 8 carbon atoms.

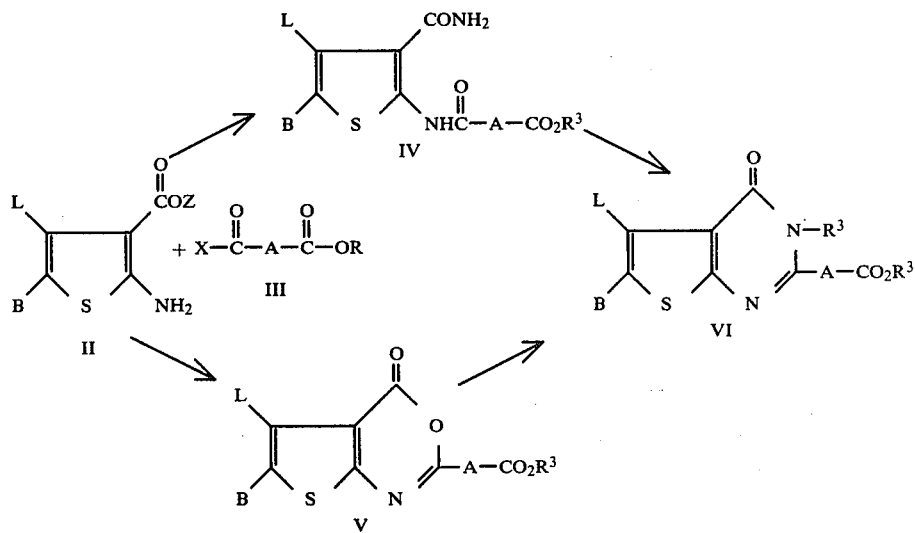

The intermediate 2-aminothiophene-3-carboxamides or 2-aminothiophene-3-carboxylic acids of Formula II on reaction with an acylating agent of Formula III yield the thiophene derivatives of Formula IV or the oxazine derivatives of Formula V. $R^3$ in Formulas IV, V, and VI is H, lower alkyl having 1 to 8 carbon atoms, or M wherein M is a nontoxic pharmacologically acceptable metal cation. The acylating agent of Formula III is an oxalic or 1,4-but-2-enedioic acid derivative. That is, A in the above formulas is either a covalent bond directly linking the indicated groups or it is the vinyl group (—CH=CH—). X is chloro, bromo, or lower alkoxy having 1 to 8 carbon atoms and is preferably the ethoxy group when operating on a starting material of Formula II wherein Z is —OH, and chloro when operating on a starting material of Formula II wherein Z is —$NH_2$.

For preparation of those substances of Formulas V and VI wherein A is the vinyl group, it is preferred to employ the starting material of Formula II wherein Z is —OH, and employ a lower alkyl diester or a lower alkyl monoester halide of 1,4-but-2-enedioic acid as the acylating agent.

For preparation of the intermediates of Formula IV wherein $R^3$ is lower alkyl, the 2-aminothiophene-3-carboxamide of Formula II wherein Z is —$NH_2$ is treated in pyridine or other aprotic solvent such as acetonitrile, benzene, or di-isopropyl ether containing at least 1 molecular proportion of pyridine relative to the acylating reactant of Formula III which is preferably ethyl oxalyl chloride. The acylating agent is carefully mixed with the solution of the carboxamide starting material at room temperature using gradual addition of the acylating agent to the intermediate or the reverse with cooling of the reaction vessel. It is undesirable to precool the reactants before commencement of the reaction. After the reaction subsides, a period of stirring at room temperature is usually employed as a precaution to allow completion of the reaction. The intermediate of Formula IV is then recovered from the reaction mixture by pouring it into a protic solvent such as isopropanol and collecting the precipitated intermediate by filtration.

The thienyl intermediates of Formula IV are novel compounds having anti-allergic activity, and are considered part of the present invention. The thienyl compounds of Formula IV wherein $R^3$ is lower alkyl are converted to the thienopyrimidines of the present invention having Formula VI by heating in the molten state at a temperature in the range of about 200°–265° C., preferably the latter. The progress of the reaction can be estimated by the foaming which occurs due to vaporization of the water formed in the process as a by-product. In each specific instance the optimum temperature for carrying out the pyrolysis can be estimated by visualization of the molten material when heated in a test tube and determining the temperature at which vigorous evolution of water vapor occurs.

The oxazines of Formula V are novel compounds having antiallergic activity and are considered part of the present invention. The oxazines of Formula V wherein $R^3$ is lower alkyl are prepared by reaction of a 2-aminothiophene-3-carboxylic acid of Formula II wherein Z is —OH with an acylating agent of Formula III under much the same conditions as those described above for the preparation of the intermediates of Formula IV. In this instance it is preferred to employ two molecular portions of the acylating agent. If a single molecular portion of acylating agent is employed, a mixture containing the intermediate 2-carbamylthiophene-3-carboxylic acid analogous in structure to the thiophene carboxamides of Formula IV may be obtained. The 2-carbamylthiophene-3-carboxylic acid may be cyclized to the oxazine of Formula V by treatment with an additional molecular proportion of the acylating agent of Formula III or other cyclodehydrating agent such as $SOCl_2$. While stepwise operation in this fashion is possible, there is no advantage. It is preferable to employ two molecular portions of Formula III acylating agent in the first instance, and to obtain the pure oxazine as the reaction product.

The oxazines of Formula V are converted to the thienopyrimidines of Formula VI by reaction with an amine of the formula RNH$_2$ wherein R is as defined above or an ammonium salt which is soluble in the reaction medium. A protic solvent, and preferably a lower alkanol such as ethanol or isopropanol, is employed as reaction medium. The reaction is carried out at the reflux temperature and the product usually crystallizes from the reaction mixture on cooling. Suitable ammonium salts are: ammonium benzenesulfonate, ammonium fluoride, ammonium fluorosulfonate, ammonium fluosilicate, ammonium acetate, ammonium iodide, ammonium nitrate, ammonium hypophosphite, and ammonium valerate. It is preferred to employ ammonium acetate optionally in the presence of approximately one chemical equivalent of acetic acid to form a buffer system and minimize amide formation from the 2-carboxy ester group.

The compounds of Formula I and VI wherein R$^3$ is H or M are prepared by hydrolysis and neutralization of the corresponding esters (R$^3$ is lower alkyl) as is exmplified in Procedures 3 and 32. The compounds of Formula IV in which R$^3$ is H or M are sometimes obtained as by-products in the preparation of the Formula VI compounds from the Formula II compounds. They may also be prepared by hydrolysis and neutralization of a Formula IV compound in which R$^3$ is lower alkyl. The compounds of Formula V wherein R$^3$ is H may be prepared by selective hydrolysis of the corresponding acid halide, and the M salts then formed by neutralization.

The compounds of Formula VI constitute a subgroup of the compounds of Formula I wherein R$^2$ is CO$_2$R$^3$ or CH=CHCO$_2$R$^3$, and R$^5$ and R$^6$ of Formula I correspond in part respectively to L and B of Formula VI. They serve as intermediates for other compounds of Formula I wherein R$^5$ and R$^6$ are hydroxy, alkoxy, nitro, amino, or halogen, or wherein R$^2$ is

5-tetrazolyl, N-(tetrazol-5-yl)carbamyl, or CHO. Conventional aromatic substitution reactions known to be operable on substituted thiophenes may be employed on Formula VI compounds wherein one of L and B is hydrogen to introduce the R$^5$ or R$^6$ group. For example, a compound of Formula I wherein R$^5$ or R$^6$ is the nitro group is prepared by nitration of the corresponding compound wherein R$^5$ or R$^6$, respectively, is a hydrogen atom, by treatment of a solution thereof in trichloroacetic acid and acetic anhydride with a solution of nitric acid in trichloroacetic acid. The reaction is carried out by a careful addition of the nitrating solution to the reactant solution at a temperature of about $-15°$ C. Any temperature from about 0° to $-20°$ C. may be employed which is convenient. The nitrothiophene is recovered from the reaction mixture by quenching with water and filtering the resulting precipitate. The resulting compound of Formula I wherein one of R$^5$ and R$^6$ is a nitro group may then be converted to the corresponding amino compound by conventional hydrogenation processes such as atmospheric pressure hydrogenation over a carbon-supported palladium catalyst employing a solvent medium for contact of the hydrogen with the catalyst and reactant.

The compounds of Formula I wherein one of R$^5$ and R$^6$ is the amino group may be converted by diazotization and replacement of the diazonium group with a halogen atom or a hydroxyl group according to known reaction conditions. For instance, the amino compound may be dissolved in aqueous fluoboric acid and treated with sodium nitrite at ice temperature to yield the corresponding diazonium fluoborate salt. The latter on treatment with cuprous chloride, bromide, or iodide yields the corresponding compound of Formula I wherein R$^5$ or R$^6$ is chloro, bromo, or iodo. The diazonium fluoborate salts may also be converted to the corresponding fluoro derivatives where one of R$^5$ and R$^6$ is the fluoro group by heating at a temperature just above the melting point (standard Scheimann reaction conditions). The iodo compounds may also be prepared by mercuration of a compound of Formula VI wherein L or B is hydrogen by reaction with mercuric acetate and treatment of the mercury derivative with iodine and potassium iodide.

The compounds of Formula I wherein one of R$^5$ and R$^6$ is hydroxy are prepared from the intermediate diazonium fluoborate salts by hydrolysis thereof, preferably with potassium trichloroacetate in trichloroacetic acid followed by treatment of the reaction product with water. The hydroxy compounds are converted to alkoxy compounds under conventional alkylation conditions such as reaction with a diazoalkane, alkyl iodide, or dialkyl sulfate.

The compounds of Formula I in which R$^2$ is the hydroxymethyl group or an ester thereof are prepared from the compounds of Formula I wherein R$^2$ is CO$_2$R by reduction with a borohydride derivative such as lithium borohydride or sodium borohydride. Again, conventional conditions involving contacting the reactants in a reaction inert solvent medium are employed. The compounds of Formula I wherein R$^2$ is the carboxaldehyde group are prepared from the corresponding hydroxymethyl compounds by oxidation, for instance, with manganese dioxide or dimethylsulfoxide in dicyclohexylcarbondiimide under known conditions.

To sum up, the compounds of Formula I are prepared by means of a process which comprises reacting a compound of Formula II with an acylating agent of Formula III to provide a compound of Formula IV or Formula V. The compound of Formula IV is then converted into a compound of Formula I by heating in the molten state at a temperature in the range of 200°–265° C. for from 5 to 15 min. The compound of Formula V is converted into a compound of Formula I by treatment in solution with an amine of the formula R$^3$NH$_2$ or a soluble ammonium salt employing a protic solvent such as a lower alkanol having 1 to 4 carbon atoms as reaction medium at the reflux temperature. The compound of Formula I thus produced corresponds to the subgroup defined by Formula VI above.

If desired, a compound of Formula VI in which one of L or B is hydrogen, may be converted to the corresponding nitro compound by nitration under conditions which are known to be operable for the preparation of nitro substituted thiophene compounds by direct nitration of the corresponding unsubstituted thiophene compound. The resulting compound of Formula I in which R$^5$ or R$^6$ is nitro is then converted by catalytic hydrogenation of the nitro group to yield a compound of Formula I in which R$^5$ or R$^6$ is amino. The latter may then be diazotized to form the corresponding diazonium salt, such as the fluoborate salt, which in turn may be reacted with a cuprous halide to provide a compound of Formula I wherein $R^5$ or $R^6$ is Cl, Br, or I or the diazonium salt may be hydrolyzed to yield the compound of Formula I wherein one of $R^5$ or $R^6$ is hydroxyl. The diazonium fluoborate salt may also be heated to its decomposition point to yield the compound of Formula I wherein one of $R^5$ or $R^6$ is fluoro. The hydroxy derivative may be etherified under conventional conditions for the formation of aromatic ethers to yield the compound of Formula I wherein $R^5$ or $R^6$ is a lower alkoxy group having 1 to 6 carbon atoms. Further, a compound of Formula I in which $R^5$ or $R^6$ is hydrogen may be converted by known methods to the mercuric acetate derivative and thence to the corresponding compound where $R^5$ or $R^6$ is iodo by treatmemt of the mercuric acetate derivative with $I_2$ and KI. This is illustrated in the following flow sheet.

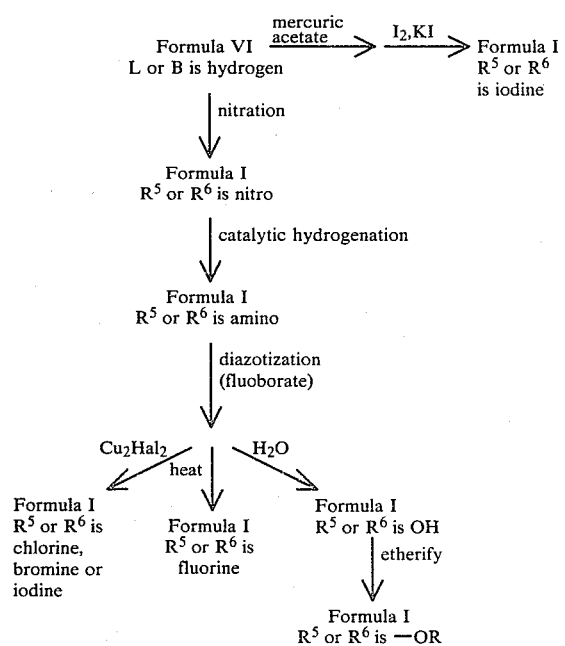

Any of the foregoing compounds of Formula VI in which A is a covalent bond linking the $CO_2R$ group to the ring may be transformed into a compound of Formula I in which $R^2$ is 5-tetrazolyl or N-(tetrazol-5-yl)-carbamoyl according to the following reaction scheme in which R, $R^5$ and $R^6$ have the same meaning as previously.

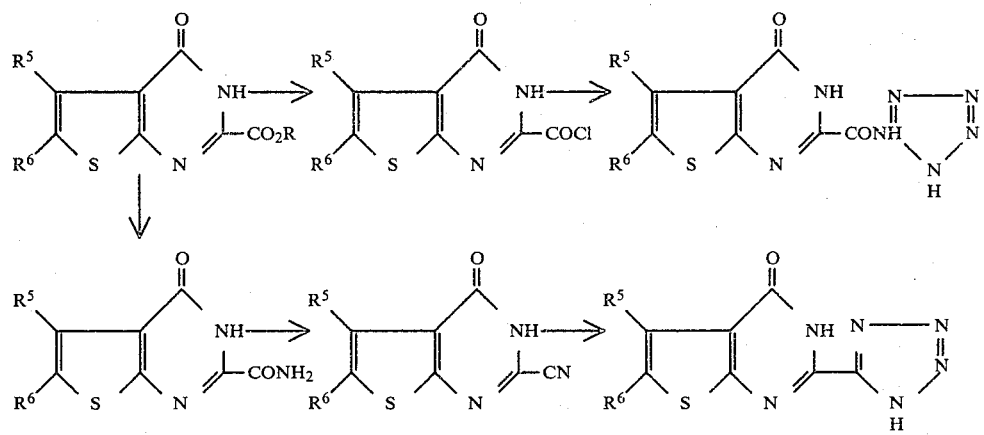

DESCRIPTION OF SPECIFIC EMBODIMENTS

The nuclear magnetic resonance spectral characteristics reported in the following procedures refer to the chemical shifts ($\delta$) expressed as parts per million (ppm) versus tetramethylsilane as reference standard except in those instances where $D_2O$ is indicated as solvent where the HDO line at 4.70 ppm was employed. The relative area reported for the various shifts corresponds to the number of hydrogen atoms in the involved substituent, and the nature of the shift as to multiplicity is reported as broad singlet (bs), singlet (s), multiplet (m), doublet (d), triplet (t), or quadruplet (q) with coupling constant (J value) reported where appropriate. The format is NMR (solvent): $\delta$(multiplicity, relative area, J value). Abbreviations for the solvents are $CDCl_3$ (deuterochloroform), DMSO-$d_6$ (deuterodimethylsulfoxide), $CF_3CO_2H$ (trifluoroacetic acid), and $D_2O$ (deuterium oxide). The infrared spectral data is a listing of the wavelengths in cm.$^{-1}$ of absorption maxima which are characteristic of functional groups. The infrared spectra were determined on potassium bromide pellets containing 0.5% of the experimental substance.

Procedure 1. ETHYL
N-[3-(AMINOCARBONYL)-4,5,6,7-TETRAHYDROBENZO[b]THIEN-2-YL]OXAMATE A suspension of 72.92 grams (0.41 mole) of 2-amino-4,5,6,7-tetrahydrobenzo[b]thiophene-3-carboxamide in 200 ml. of dry pyridine is stirred at 25° C. during the addition of 55.25 grams (0.41 mole) of ethyl oxalyl chloride dissolved in 50 ml. of dry acetonitrile in drop-wise fashion. Cooling of the reaction vessel by immersion in ice water is employed and the flask is kept in the ice bath for 30 min. after the addition is complete. The reaction vessel should not be pre-cooled before commencement of the addition of the ethyl oxalyl chloride. After the reaction is complete and the ice bath is removed, 150 ml. of the acetonitrile is added to the reaction mixture to facilitate stirring, and the mixture is kept overnight with stirring. It is then poured into isopropanol and the precipitated product is collected on a filter. The product is air dried, yielding 58.80 g. (49%) of a yellow solid, m.p. 204.0°–205.0° C. A sample of this material recrystallized from isopropanol exhibited the same melting point.

NMR (DMSO-d$_6$): 12.88 (s,1), 7.30 (s,2), 4.37 (q,2), 2.70 (m,4), 1.75 (m,4), 1.37 (t,3). Infrared (KBr): 1635, 1680, and 1720 cm.$^{-1}$.

Anal. found: C, 52.68; H, 5.34; N, 9.42.

Procedure 2. ETHYL 3,4,5,6,7,8-HEXAHYDRO-4-OXOBENZO-THIENO[2,3-d]PYRIMIDINE-2-CARBOXYLATE The product of Procedure 1, 8.89 g. (0.030 mole) is melted in a round bottom flask equipped with a magnetic stirring bar and immersed in an oil bath at 261° C. The molten material is heated with stirring until the evolution of water as is evidenced by bubbling of the reaction mixture is no longer evident. About 5–15 min. is sufficient. The molten mass is then dissolved in dimethylformamide and the warm solution is poured into a volume of methanol larger than the reaction mixture. The precipitate is collected, and recrystallized from a mixture of dimethylformamide and methanol to yield 4.92 g. (48%) of the desired product as fine yellow needles, m.p. 207.0°–209.0° C.

NMR (CDCl$_3$): 10.35 (bs,1), 4.50 (q,2, J=7.0 Hz), 2.90 (m,4), 1.88 (m,4), 1.47 (t,3). Infrared (KBr): 3110, 3030, 2940, 1740, 1670, 1570, 1490, 1465, 1370, 1365, 1300, 1187, and 1035 cm.$^{-1}$. Ultraviolet absorption maxima (0.1 N-HCl) 255, 348 mµ; (0.1 N-NaOH) 275, and 311 mµ.

Anal. found: C, 55.92; H, 5.53; N, 10.04.

Procedure 3. 3,4,5,6,7,8-HEXAHYDRO-4-OXOBENZO-THIENO[2,3-d]-PYRIMIDINE-2-CARBOXYLIC ACID DISODIUM SALT DIHYDRATE C$_{11}$H$_{10}$N$_2$O$_3$S.2Na.2H$_2$O The product of Procedure 2, 12.0 g. (0.043 mole) and 4.0 g. (0.10 mole) of sodium hydroxide is dissolved in a mixture of 440 ml. of water and 160 ml. of ethanol and heated on a steam bath until dissolved. Following dissolution of the starting material, there is a transient precipitation of the monosodium salt of the product. This material redissolves as heating is continued until a clear solution finally results. The solution is stirred at room temperature for 6 hrs. while the desired disodium salt precipitates. The product is collected on a filter and air-dried, yield 10.4 g. (73%). This product failed to melt on heating in a capillary tube at 355° C.

NMR (DMSO-d$_6$): 2.81 (m,4), 1.78 (m,4). Infrared (KBr): 2940, 1630, 1580, 1550, 1490, 1435, 1390, 1350, 1320, 1275, 1050, 810, and 768 cm.$^{-1}$.

Anal. found: C, 40.27; H, 3.63; N, 8.40.

Procedure 4. ETHYL 5-METHYL-6-OCTYL-4-OXO-4H-THIENO[2,3-d][1,3]OXAZINE-2-CARBOXYLATE To a suspension of 2-amino-4-methyl-5-(n-octyl)thiophene-3-carboxylic acid hydrate ($\frac{1}{4}$H$_2$O), 6.88 g. (0.025 mole), in 25 ml. of dry pyridine which is first cooled to 0° C. there is added 6.92 g. (0.051 mole) of ethyl oxalyl chloride in drop-wise fashion. The mixture is stirred at 25° C. for 1 hr. after the addition is complete and then poured into 1 l. of cold water. The product precipitates and is recovered by extraction with octane; yield 6.4 g. (73%), recrystallized from low boilig petroleum ether, white crystals, m.p. 66.0°–69.0° C.

NMR (CDCl$_3$): 4.48 (q,2, J=7.1 Hz), 2.81 (t,2, J=6.8 Hz), 2.45 (s,3), 1.44 (t,3, J=7.1 Hz), 1.28 (m,12), and 0.88 (m,3). Infrared (KBr): 2960, 2930, 2860, 1765, 1742, 1588, 1468, 1448, 1368, 1310, 1198, 1150, 1100, 1020, and 770 cm.$^{-1}$.

Anal. found: C, 61.48; H, 7.21; N, 3.89.

Procedure 4 may be modified by employing 2-[[(ethoxycarbonyl)carbonyl]amino]-4-methyl-5-octylthiophene-3-carboxylic acid as starting material and employing one equivalent of ethyl oxalyl chloride to effect the cyclization.

Procedure 5. ETHYL 3,4-DIHYDRO-5-METHYL-6-OCTYL-4-OXO-THIENO[2,3-d]PYRIMIDINE-2-CARBOXYLATE A mixture of 5.54 g. (0.016 mole) of the product of Procedure 4, 1.10 g. (0.0143 mole) of ammonium acetate, and 0.385 g. (0.0064 mole) of acetic acid in 50 ml. of absolute ethanol is heated on a steam bath for 40 min. Upon cooling, the desired product crystallizes in the form of needles which are collected on a filter and dried, yield 4.39 g. (79%). After recrystallization from isopropanol, the material was obtained as off-white needles, m.p. 136.0°–137.0° C.

NMR (CDCl$_3$): 4.51(q,2, J=7.1 Hz), 2.80(t,2, J=6.8 Hz), 2.53(s,3), 1.46(t,3, J=7.1 Hz), 1.30(m,12), 0.89(m,3).

Infrared (KBr): 3180, 3100, 3040, 2925, 2850, 1740, 1680, 1570, 1492, 1470, 1370, 1305, 1193, and 1033 cm.$^{-1}$.

Anal. found: C, 61.53; H, 7.37; N, 8.01.

Procedures 6–12. Additional Thienyloxamates. By adaptation of the method of Procedure 1 to the appropriately substituted 2-aminothiophene-3-carboxamides, the following correspondingly substituted ethyl N-[3-(aminocarbonyl)thien-2-yl]oxamates are prepared. The physical properties and recrystallization solvents are noted following the name of each of these substances in Table I.

TABLE I

| | Thienyloxamates |
|---|---|
| Procedure No. | Name |
| 6 | ETHYL [3-(AMINOCARBONYL)-5-PHENYLTHIEN-2-YL]OXAMATE. Recrystallized from ethanol-isopropanol, m.p. 198°–200° C. Anal. found: C, 56.70; H, 4.56; N, 8.87 |
| 7 | ETHYL N-[3-(AMINOCARBONYL)-4-METHYL-5-PHENYLTHIEN-2-YL]-OXAMATE.- Recrystallized from dimethylformamide-ethanol, m.p. 175°–176° C. |
| 8 | ETHYL N-[3-(AMINOCARBONYL)-5-HEXYL-4-METHYLTHIEN-2-YL]-OXAMATE.- Recrystallized from isopropyl acetate-isopropyl ether, m.p. 147°–149° C. Anal. found: C, 56.31; H, 7.24; N, 8.25 Hydrolysis of this substance yields N-[3-Aminocarbonyl)-5-hexyl-4-methylthien-2-yl]oxamic acid sodium salt, |

TABLE I-continued

Thienyloxamates

| Procedure No. | Name |
|---|---|
| | $C_{14}H_{20}N_2O_4S$ . Na salt, m.p. > 350° C. |
| 9 | ETHYL N-[3-(AMINOCARBONYL)-4-METHYLTHIEN-2-YL]OXAMATE.- Recrystallized from dimethylformamide-absolute ethanol, m.p. 196°-198° C. Anal. found: C, 46.86; H, 4.78; N, 10.76. |
| 10 | ETHYL N-[3-(AMINOCARBONYL)-4-METHYL-5-PENTYLTHIEN-2-YL]OXAMATE.- Recrystallized from isopropanol, m.p. 153°-154° C. |
| 11 | ETHYL N-[3-(AMINOCARBONYL)-4-METHYL-5-(3-METHYL-2-BUTENYL)-2-YL]OXAMATE. -Recrystallized from isopropanol, m.p. 199°-200° C. |
| 12 | ETHYL N[3-(AMINOCARBONYL)-6-tert-BUTYL-4,5,6,7-TETRA-HYDROBENZO[b]THIEN-2-YL]OXAMATE.- Recrystallized from chloroform-ethanol, m.p. 228.5°-231.5° C. Anal. found: C, 58.28; H, 7.03; N, 7.80 |

Procedures 13–19. Additional Thienopyrimidine-2-Carboxylates by Cyclization of Thienyloxamates The products of the present invention, which are listed in Table II, were prepared by heating the molten thienyloxamates listed in Table I according to the method of Procedure 2 above. In Table II the figure in parenthesis following the Procedure No. is the procedure number for the preparation of the starting material employed.

TABLE II

Thienopyrimidine-2-Carboxlates

| Procedure No. | Name |
|---|---|
| 13 (6) | ETHYL 3,4-DIHYDRO-4-OXO-6-PHENYLTHIENO[2,3-d]PYRIMIDINE-2-CARBOXYLATE.-Recrystallized from acetonitrile, yellow crystalline solid, m.p. 228.0°-232.0° C. NMR (CDCl$_3$): 10.80 (bs,1), 7.71 (s,l), 7.45 (m,5), 4.52 (q,2, J = 7.0 Hz), and 1.48 (t,3, J =7.0 Hz,). Infrared (KBr): 3440, 3090, 3050, 1720, 1667, 1560, 1468, 1440, 1365, 1178, 1030, 840, 750, and 684 cm.$^{-1}$. Anal. found: C, 59.87; H, 4.03; N, 9.32. |
| 14 (7) | ETHEL 3,4-DIHYDRO-5-METHYL-4-OXO-6-PHENTYLTHIENO[2,3-d]-PYRIMIDINE-2-CARBOXYLATE.- Recrystallized from dimethylformamide-ethanol, m.p. 225.5°-227.5° C., yellow crystalline solid. NMR (CDCl$_3$): 10.40 (bs,1), 7.39 (m,5), 4.51 (q,2, J = 7.1 Hz), 2.65 (s,3), 1.47 (t.3, J = 7.1 Hz). Infrared (KBr): 3160, 3090, 3020, 2980, 2930, 1727, 1665, 1565, 1480, 1368, 1300, 1175, 1030, 1005, 778, 760, 737 and 695 cm.$^{-1}$. Anal. found: C, 61.02; H, 4.38; N, 8.87. |
| 15 (8) | ETHYL 3,4-DIHYDRO-6-HEXYL-5-METHYL-4-OXOTHIENO[2,3-d]-PYRIMIDINE-2-CARBOXYLATE.- Recrystallized from isopropanol, yellow needles, m.p. 134.0°-135.0° C. NMR (CDCl$_3$): 10.33 (bs,1), 4.49 (q.2, J= 7.1 Hz), 2.79 (t,2, J = 7.0 Hz), 2.50 (s,3), 1.43 (t,3, J = 7.1 Hz), 1.36 (m,8), 0.88 (m,3). Infrared (KBr): 3100, 2020, 2840, 1734, 1672, 1565, 1488, 1460, 1365, 1300, 1185, and 1030 cm.$^{-1}$. Anal. found: C, 59.90; H, 6.92; N, 8.61. |
| 16 (9) | ETHYL 3,4-DIHYDRO-5-METHYL-4-OXOTHIENO[2,3-d]PYRIMIDINE-2-CARBOXYLATE.- Recrystallized from ethanol, pale yellow crystals, m.p. 151.5°-162.0° C. NMR (DMS0-d$_6$): 12.50 (bs,1), 7.33 (q,1, J = 1.1 Hz), 4.37 (q,2, J = 7.1 Hz), 2.50 (d,3, J = 1.1 Hz,) and 1.35 (t,3, J = 7.1 Hz). Infrared (KBr): 3180, 3080, 1732, 1672, 1570, 1490, 1370, 1300, 1285, 1180, 1155, 1035, and 1010 cm.$^{-1}$. Anal. found: C, 50.24; H, 4.22; N, 11.72. |
| 17 (10) | ETHYL 3,4-DIHYDRO-5-METHYL-4-OXO-6-PENTYLTHIENO[2,3-d]-PYRIMIDINE-2-CARBOXYLATE.- Recrystallized from isopropanol, olive-green crystals, m.p. 152.5°-153.5° C. NMR (CDCl$_3$): 9.80 (bs,1), 4.52 (q,2, J = 7.2 Hz), 2.81 (t,2, J = 6.5 Hz), 2.52 (s,3), 1.46 (t,3, J = 7.2 Hz) 1.38 (m,6), and 0.91 (m,3). Infrared (KBr): 3080, 3020, 2950, 2920, 2842, 1738, 1675, 1568, 1490, 1365, 1300, 1090, and 1030 cm.$^{-1}$. Anal. found: C, 58.42; H, 6.65; N, 9.19. |
| 18 (11) | ETHYL 3,4-DIHYDRO-5-METHYL-6-(3-METHYL-2-BUTENYL)-4-OXOTHIENO[2,3-d]PYRIMIDINE-2-CARBOXYLATE.- Chromatographed on silica gel and eluted with chloroform. Evaporation of solvent yielded an oil with failed to crystallize. The nuclear magnetic resonance spectrum indicated that the product was a mixture of the above named compound and the -6-(3-methyl-1-butenyl)isomer. |

TABLE II-continued

Thienopyrimidine-2-Carboxlates

| Procedure No. | Name |
|---|---|
| 19 (12) | ETHYL 7-t-BUTYL-3,4,5,6,7,8-HEXAHYDRO-4-OXOBENZOTHIENO-[2,3-d]PYRIMIDINE-2-CARBOXYLATE.- Chromatographed on silica gel (hexane) and eluted with ether. Recrystallized from isopropanol, pale yellow powder, m.p. 180.0°–183.0° C.<br>NMR (CDCl$_3$): 10.30 (bs,1), 4.50 (q,2, J = 7.1 Hz), and 0.95 (s,9).<br>Infrared (KBr): 2930, 1730, 1662, 1362, 1300, 1281, 1180, and 1092 cm.$^{-1}$.<br>Anal. found: C, 61.30; H, 6.60; N, 8.35. |

Procedures 20–26. Thienooxazine-2-carboxylic Acids

The following thienooxazines are prepared by substitution of the appropriately substituted 2-aminothiophene-3-carboxylic acids in the method of Procedure 4. The thienooxazines are listed in Table III with their physical properties and procedural modifications where such are required.

TABLE III

Thienooxazine-2-Carboxylic Acids

| Procedure No. | Name |
|---|---|
| 20 | ETHYL 5,6,7,8-TETRAHYDRO-4-OXO-4H-BENZOTHIENO[2,3-d]-[1,3]OXAZINE-2-CARBOXYLATE. Recrystallized from isopropyl acetate as the hydrate ($\frac{1}{4}$ H$_2$O), yellow solid, m.p. 148.5°–180.5° C.<br>NMR (DMSO-d$_6$): 4.32 (q,2, J = 7.1 Hz), 2.79 (m,4), 1.79 (m,4) and 1.33 (t,3, J = 7.1 Hz).<br>Infrared (KBr): 2990, 2950, 2880, 1767, 1740, 1640, 1582, 1560, 1460, 1372, 1350, 1300, 1185, 1150, 1090, 1020, and 768 cm.$^{-1}$.<br>Anal. found: C, 55.23; H, 5.06; N, 4.96. |
| 21 | ETHYL 6-ETHYL-5-METHYL-4-OXO-4H-THIENO[2,3-d][1,3]-OXAZINE-2-CARBOXYLATE.- 1:1 pyridine-acetonitrile was used as reaction medium; chromatographed on silica gel (CHCl$_3$): recrystallized from isopropyl ether, light yellow needles, m.p. 97.5°–99.5° C.<br>NMR (DMSO-d$_6$): 4.36 (q,2, J = 7.1 Hz), 2.88 (q,2, J = 7.1 Hz), 2.38 (s,3), 1.32 (t,3, J = 7.1 Hz), and 1.22 (t,3, J = 7.2 Hz).<br>Infrared (KBr): 2980, 1778, 1760, 1590, 1544, 1470, 1450, 1390, 1320, 1275, 1210, 1170, 1110, 1025, 954, 924, 915, and 771 cm.$^{-1}$.<br>Anal. found: C, 54.27; H, 4.94; N, 5.13. |
| 22 | ETHYL 5-METHYL-6-(2-METHYLPROPYL)-4-OXO-4H-THIENO[2,3-d]-[1,3]OXAZINE-2-CARBOXYLATE.- Recrystallized hexane, m.p. 78.5°–79.5° C.<br>NMR (DMSO-d$_6$): 4.35 (q,2, J = 7.0 Hz), 2.72 (d,2, J = 6.8 Hz), 2.38 (s,3), 1.87 (m,1), 1.32 (t,3, J = 7.0 Hz), and 0.92 (d,6, J = 6.5 Hz).<br>Infrared (KBr): 2960, 2935, 2880, 1764, 1740, 1592, 1470, 1374, 1320, 1196, 1160, 1102, and 770 cm.$^{-1}$.<br>Anal. found: C, 57.31; H, 5.77; N, 4.84. |
| 23 | ETHYL 6-ETHYL-4-OXO-4H-THIENO[2,3-d][1,3]OXAZINE-2-CARBOXYLATE.- 13:1 acetonitrile-pyridine was used as reaction medium; recrystallized from ethyl acetate-low boiling petroleum ether, light yellow needles, m.p. 109.0°–111.0° C.<br>NMR (CDCl$_3$): 7.18 (m,1), 4.48 (q,2, J = 7.1 Hz), 2.92 (m,2), 1.43 (t,3, J = 7.1 Hz), and 1.36 (t,3, J = 7.2 Hz).<br>Infrared (KBr): 3110, 3000, 1982, 1773, 1752, 1590, 1540, 1375, 1331, 1314, 1215, 1172, 1090, 844, and 769 cm.$^{-1}$.<br>Anal. found: C, 51.93; H, 4.26; N, 5.55. |
| 24 | ETHYL 6-ACETYL-5-METHYL-4-OXO-4H-THIENO[2,3-d][1,3]-OXAZINE-2-CARBOXYLATE.- 3:8 pyridine-acetonitrile was used as reaction medium; chromatographed on silica gel (CHCl$_3$), recrystallized chloroform-hexane, pale yellow platelets, m.p. 102.0°–103.0° C.<br>NMR (CDCl$_3$): 4.50 (q,2, J = 7.1 Hz), 2.89 (s,3), 2.62 (s,3), 1.46 (t,3, J = 7.1 Hz).<br>Infrared (KBr): 2992, 1770, 1752, 1671, 1594, 1510, 1312, 1274, 1238, 1188, 1131, 929, 770, and 574 cm.$^{-1}$.<br>Anal. found: C, 51.03; H, 3.92, N, 4.86. |
| 25 | ETHYL 3,4-DIHYDRO-5,6-DIMETHYL-4-OXOTHIENO[2,3-d][1,3]-OXAZINE-2-CARBOXYLATE.- 2:1 pyridine-acetonitrile was used as reaction medium; recrystallized ethanol, dark brown crystals, m.p. 129°–130° C.<br>NMR (CDCl$_3$): 4.409 (q, 2, J = 7.2 Hz), 2.44 (s,6), 1.44 (t,3, J = 7.2 Hz). |

TABLE III-continued

Thienooxazine-2-Carboxylic Acids

| Procedure No. | Name |
|---|---|
| | Infrared (KBr): 3002, 2980, 1774, 1748, 1590, 1554, 1460, 1372, 1322, 1294, 1208, 1170, 1110, 1030, 958, 872, and 775 cm$^{-1}$.<br>Anal. found: C, 51.95; H, 4.49; N, 5.30. |
| 26 | ETHYL 6-HEXYL-5-METHYL-4-OXO-4H-THIENO[2,3-d][1,3]-OXAZINE-2-CARBOXYLATE.- 5:1 acetonitrile-pyridine was used as reaction medium; recrystallized from low boiling petroleum ether-ethyl ether, light tan solid, m.p. 56.5°-57.0° C.<br>NMR (CDCl$_3$): 4.63 (q,2, J = 7.0 Hz), 2.92 (t,2, J = 6.8 Hz), 2.47 (s,3), 1.46 (t,3, J = 7.0 Hz), 1.36 (m,8), and 0.90 (m,3).<br>Infrared (KBr): 2950, 2920, 2850, 1750, 1580, 1465, 1440, 1370, 1318, 1278, 1205, 1160, 1096, 1016, 920, 906, and 765 cm.$^{-1}$.<br>Anal. found: C, 59.44; H, 6.42; N, 4.26; S, 10.01 |

Procedures 27–31. Additional Thienopyrimidine-2-carboxylates From Thieno-oxazine-2-carboxylates The method of Procedure 5 is adapted to the preparation of the compounds listed in Table IV by substitution of the appropriately substituted thieno-oxazine-2-carboxylate as starting material. The products produced are identified in Table IV along with information as to purification and identification. The number in parenthesis next to the Procedure No. identifies the procedure for preparation of the starting material. The starting materials are listed in Table III.

TABLE IV

Thienopyrimidine-2-Carboxylates

| Procedure No. | Name |
|---|---|
| 27 (21) | ETHYL 6-ETHYL-3,4-DIHYDRO-5-METHYL-4-OXOTHIENO[2,3-d]-PYRIMIDINE-2-CARBOXYLATE.- Recrystallized from absolute ethanol, white flakes, m.p. 148.5°-173.5° C.<br>NMR (CDCl$_3$): 4.51 (q,2, J = 7.1 Hz), 2.85 (q,2 J = 7.3 Hz), 2.25 (s,3), 1.46 (t,3, J = 7.1 Hz), and 1.30 (t,3, J = 7.3 Hz).<br>Infrared (KBr): 3180, 3100, 2060, 2930, 1730, 1680, 1555, 1488, 1460, 1368, 1300, 1186, and 1032 cm.$^{-1}$.<br>Anal. found: C, 54.17; H, 5.50; N, 10.029. |
| 28 (22) | ETHYL 3,4-DIHYDRO-5-METHYL-6-(2-METHYLPROPYL)-4-OXOTHIENO-[2,3-d]PYRIMIDINE-2-CARBOXYLATE.- Recrystallized from isopropanol, off-white crystals, m.p. 175°-176° C.<br>NMR (DMSO-d$_6$): 12.40 (bs,1), 4.36 (q,2, J = 7.1 Hz), 2.68 (d,2, J = 6.7 Hz), 2.43 (s,3), 1.88 (m,1), 1.34 (t,3, J = 7.1 Hz), and 0.92 (d,6, J = 6.5 Hz).<br>Infrared (KBr): 3090, 2960, 2930, 2870, 1740, 1675, 1570, 1490, 1467, 1383, 1369, 1305, 1194, 1034, and 768 cm$^{-1}$.<br>Anal. found: |
| 29 (23) | ETHYL 6-ETHYL-3,4-DIHYDRO-4-OXOTHIENO[2,3-d]PYRIMIDINE-2-CARBOXYLATE.- Recrystallized from ethanol, pale yellow needles, m.p. 163.0°-168.0° C.<br>NMR (CDCl$_3$): 10.30 (bs,1), 7.26 (t,1, J = 1.1 Hz), 4.55 (q,2, J = 7.0 Hz), 2.92 (m,2), 1.48 (t,3, J = 7.0 Hz) and 1.38 (t,3, J = 7.2 Hz).<br>Infrared (KBr): 3180, 3120, 3045, 2980, 2945, 2890, 1749, 1694, 1579, 1949, 1376, 1315, 1194, 1046, 852, 848, and 770 cm$^{-1}$.<br>Anal. found: C, 52.48; H, 4.84; N, 11.21. |
| 30 (24) | ETHYL 6-ACETYL-3,4-DIHYDRO-5-METHYL-4-OXOTHIENO[2,3-d]-PYRIMIDINE-2-CARBOXYLATE.- Recrystallized from dimethylformamide-ethanol, off-white needles, m.p. 236.0°-242.0° C.<br>NMR (DMSO-d$_6$): 12.30 (bs,1), 4.38 (q,2, J = 7.0 Hz), 2.84 (s,3), 2.58 (s,3) and 1.35 (t,3, J = 7.0 Hz).<br>Infrared (KBr): 3100, 2980, 1732, 1697, 1665, 1572, 1512, 1430, 1368, 1310, 1233, 1185, and 1027 cm.$^{-1}$.<br>Anal. found C, 51.17; H, 4.15; N, 9.90. |
| 31 (25) | ETHYL 3,4-DIHYDRO-5,6-DIMETHYL-4-OXOTHIENO[2,3-d]-PYRIMIDINE-2-CARBOXYLATE.- Recrystallized from acetonitrile, brown crystalline solid, m.p. 211.5°-212.5° C.<br>NMR (CDCl$_3$): 10.60 (bs,1), 4.60 (q,2, J = 7.2 Hz), 2.54 (s,3), 2.45 (s,3), and 1.47 (t,3, J = 7.2 Hz).<br>Infrared (KBr): 3170, 3100, 2992, 2920, 1736, 1680, 1562, 1490, 1362, 1298, 1188, 1162, 1035, 1019, and 775 cm$^{-1}$.<br>Anal. found: C, 52.14; H, 4.62; N, 10.89 |

Procedure 32.
3,4,5,6,7,8-HEXAHYDRO-4-OXOBENZO-THIENO[2,3-d]PYRIMIDINE-2-CARBOXYLIC ACID MONOHYDRATE The product of Procedure 3, 5.0 g. is dissolved in 150 ml. of warm water and the solution clarified by filtration. The filtrate is acidified with glacial acetic acid and refrigerated overnight. The precipitate is collected, washed on the filter with water and dried, cream colored solid, m.p. 254.5°–256.5° C.

NMR (DMSO-$d_6$): 2.84 (m,4), 1.79 (m,4).

Infrared (KBr): 3470, 3100, 3020, 2940, 1695, 1660, 1490, 1440, 1300, 1197, 1145, 1033, 960, and 720 cm.$^{-1}$.

Anal. found: C, 49.39; H, 4.20; N, 10.33.

Procedures 33–45. Additional Thienopyrimidine-2-carboxylic Acid Metal Salts

The method of Procedure 3 is applied to various other thienopyrimidine-2-carboxylic esters with the production of various salts. The substances produced are listed in Table V along with reference to the source of the starting material identified by procedure number shown in parenthesis adjacent to the Procedure No., and the analytical information with respect to these products.

TABLE V

| Procedure No. | Salts — Name |
|---|---|
| 33 (5) | 3,4-DIHYDRO-5-METHYL-6-OCTYL-4-OXOTHIENO[2,3-d]PYRIMIDINE-2-CARBOXYLIC ACID DISODIUM SALT HYDRATE $C_{16}H_{22}N_2O_3S \cdot 2Na \cdot H_2O$. - Failed to melt at 300° C.<br>NMR (DMSO-$d_6$): 2.79 (t,2 J = 6.9 Hz.), 2.45 (s,3), 1.26 (m,12), and 0.86 (m,3).<br>Infrared (KBr): 2980, 2945, 2876, 1660, 1630, 1580, 1553, 1493, 1445, 1392, 1360, 1060, and 814 cm.$^{-1}$.<br>Anal. found: C, 49.81; H, 5.75; N, 7.05. |
| 34 (7.2 Hz), | 3,4-DIHYDRO-4-OXO-6-PHENYL-THIENO[2,3-d]PYRIMIDINE-2-CARBOXYLIC ACID SODIUM SALT HEMIHYDRATE $C_{13}H_8N_2O_3S \cdot Na \cdot \frac{1}{2}H_2O$.- Crude disodium salt prepared as in Procedure 3 was dissolved in warm water and carefully acidified with acetic acid until a white precipitate formed; white powder, m.p. 292.0°–294.0° C. (dec.).<br>NMR (DMSO-$d_6$): 7.80 (s,2), 7.71 (m,2) and 7.38 (m,3).<br>Infrared (KBr): 3430, 3230, 1660, 1465, 1440, 1360, 1290, 1180, 1040, 810, 750, 700, and 685 cm.$^{-1}$.<br>Anal. found: C, 51.61; H, 3.33; N, 9.08. |
| 35 (14) | 3,4-DIHYDRO-5-METHYL-4-OXO-PHENYLTHIENO[2,3-d]-PYRIMIDINE-2-CARBOXYLIC ACID DISODIUM SALT HYDRATE $C_{14}H_{10}N_2O_3S \cdot 2Na \cdot H_2O$. - Failed to melt at 350° C.<br>NMR (CF$_3$COOH): 7.46 (s,5), 2.71 (s,3).<br>Infrared (KBr): 3450, 2970, 2930, 1620, 1570, 1490, 1440, 1385, 1365, 1295, 1070, 1050, 810, 765, 750, and 700 cm.$^{-1}$.<br>Anal. found: C. 48.14; H, 2.83; N, 8.07. |
| 36 (15) | 6-HEXYL-3,4-DIHYDRO-5-METHYL-4-OXOTHIENO[2,3-d]-PYRIMIDINE-2-CARBOXYLIC ACID DISODIUM SALT HYDRATE $C_{14}H_{18}N_2O_3S \cdot 2Na \cdot \frac{1}{2}H_2O$. - Isopropanol added to induce precipitation; recrystallized from hot water; pale yellow solid, failed to melt at 360° C.<br>NMR (CF$_3$COOH): 3.02 (t,2, J = 6.5 Hz), 2.63 (s,3), 1.46 (m,8), and 0.94 (m,3).<br>Infrared (KBr): 2960, 2930, 2860, 1650, 1565, 1480, 1379, 1045, and 785 cm.$^{-1}$.<br>Anal. found: C, 49.31; H, 5.30; N, 8.18. |
| 37 (16) | 3,4-DIHYDRO-5-METHYL-4-OXOTHIENO[2,3-d]PYRIMIDINE-2-CARBOXYLIC ACID DISODIUM SALT DIHYDRATE $C_8H_6N_2O_3S \cdot 2Na \cdot 2H_2O$.- Product recovered by evaporation of solvent and trituration of residue with hot methanol; off-white powder, failed to melt at 300° C.<br>NMR (D$_2$O): 6.84 (m,1), 2.49 (m,3).<br>Infrared (KBr): 2940, 1660. 1630, 1582, 1539, 1510, 1490, 1439, 1390, 1380, 1350, 12980, 1076, 1055, 814, 801, 620 cm.$^{-1}$.<br>Anal. found: C, 33.40; H, 2.13; N, 9.44. |
| 38 (17) | 3,4-DIHYDRO-5-METHYL-4-OXO-6-PENTYLTHIENO[2,3-d]PYRIMIDINE-2-CARBOXYLIC ACID DISODIUM SALT SESQUIHYDRATE $C_{13}H_{16}N_2O_3S \cdot 2Na \cdot 1\frac{1}{2}H_2O$. Light yellow solid, failed to melt at 350° C.<br>NMR: 3.00 (t,2, J = 6.5 Hz), 2.62 (s,3), 1.50 (m,6) and 0.96 (m,3).<br>Infrared (KBr): 2960, 2924, 2878, 2860, 1654, 1620, 1571, 1482, 1438, 1384, 1370, 1350, 1050, and 805 cm.$^{-1}$.<br>Anal. found: C, 44.46; H, 4.85; N, 7.90. |
| 39 (18) | 3,4-DIHYDRO-5-METHYL-6-(3-METHYL-2-BUTENYL)-4-OXOTHIENO-[2,3-d]PYRIMIDINE-2-CARBOXYLIC ACID DISODIUM SALT SESQUI-HYDRATE $C_{13}H_{14}N_2O_3S \cdot 2Na \cdot 1\frac{1}{2}H_2O$. - Precipitated from reaction after evaporation of alcohol by addition of isopropanol; |

TABLE V-continued

Salts

| Procedure No. | Name |
|---|---|
| | yellow solid, failed to melt at 350° C.<br>NMR (CF$_3$COOH): 6.70 (m,2), 5.55 (m,1), 3.72 (m,3), 2.71 (s,6), 1.85 (m,6), and 1.22 (d,6, J = 6.5 Hz).<br>Infrared (KBr): 3420, 2965, 2925, 1655, 1625, 1572, 1432, 1384, 1370, 1350, 1050, and 805 cm.$^{-1}$.<br>Anal. found: C, 44.37; H, 3.94; N, 7.88. |
| 40 (19) | 7-t-BUTYL-3,4,5,6,7,8-HEXAHYDRO-4-OXOBENZOTHIENO[2,3-d]-PYRIMIDINE-2-CARBOXYLIC ACID DISODIUM SALT DIHYDRATE, C$_{15}$H$_{16}$N$_2$O$_3$S . 2Na . 2H$_2$O. - Dimethylsulfoxide sulfoxide was added to the reaction mixture for solubilization; product precipitated with isopropanol; failed to melt at 300° C.<br>NMR (CF$_3$COOH): 2.98 (m,4), 2.18 (m,2), 1.67 (m,1), and 1.02 (s,9). Infrared (KBr): 2960, 1650, 1600, 1572, 1540, 1479, 1430, 1382, 1317, 1045, and 780 cm.$^{-1}$.<br>Anal. found: C, 46.76; H, 4.92; N, 7.01. |
| 41 (25) | 3,4-DIHYDRO-5,6-DIMETHYL-4-OXOTHIENO[2,3-d]PYRIMIDINE-2-CARBOXYLIC ACID DISODIUM SALT SESQUIHYDRATE C$_9$H$_8$N$_2$O$_3$S . 2Na . 1½H$_2$O. - Product precipitated from aqueous reaction mixture with isopropanol; gray solid, failed to melt at 350° C.<br>NMR (CF$_3$COOH): 2.64 (s,6). Infrared (Kbr): 2920, 1650, 1620, 1578, 1550, 1484, 1430, 1384, 1380, 1350, 1280, 1200, 1050, and 807 cm.$^{-1}$.<br>Anal. found: C, 3665; H, 2.90; N, 9.36. |
| 42 (27) | 6-ETHYL-3,4-DIHYDRO-5-METHYL-4-OXOTHIENO[2,3-d]PYRIMIDINE-2-CARBOXYLIC ACID DISODIUM SALT DIHYDRATE C$_{10}$H$_{10}$N$_2$O$_3$S . 2Na . 2H$_2$O. - Isopropanol was added to the reaction mixture to induce crystalization of the product; white solid, failed to melt at 360° C.<br>NMR (D$_2$O): 2.95 (q,2, J = 7.2 Hz), 2.49 (s,3), 1.30 (t,3, J = 7.2 Hz). Infrared (KBr): 2975, 2940, 1650, 1620, 1570, 1540, 1484, 1435, 1386, 1355, 1320, 1278, 1050, 808 cm.$^{-1}$.<br>Anal. found: C, 37.73; H, 3.41; N, 8.46. |
| 43 (28) | 3,4-DIHYDRO-5-METHYL-6-(2-METHYLPROPYL)-4-OXOTHIENO-[2,3-d]PYRIMIDINE-2-CARBOXYLIC ACID DISODUM SALT SESQUIHYDRATE C$_{12}$H$_{14}$N$_2$O$_3$S . 2Na . 1½H$_2$O. - Product precipitated from the reaction mixture on addition of isopropanol; white solid, failed to melt at 350° C.<br>NMR (CF$_3$COOH): 2.89 (d,2, J = 7.0 Hz), 2.63 (s,3), 1.95 (m,2), 1.41 (m,1), 1.05 (d,6 J = 6.5 Hz).<br>Infrared (KBr): 2950, 2922, 2865, 1650, 1620, 1565, 1530, 1465, 1380, 1355, 1200, 1045, and 802 cm.$^{-1}$.<br>Anal. found: C, 42.81; H, 4.62; N, 8.35. |
| 44 (29) | 6-ETHYL-3,4-DIHYDRO-4-OXOTHIENO[2,3-d]PYRIMIDINE-2-ARBOXYLIC ACID DISODIUM SALT DIHYDRATE C$_9$H$_8$N$_2$O$_3$S . 2Na . 2H$_2$O. - Methanol was used as reaction solvent; white powder, failed to melt at 360° C.<br>NMR (D$_2$O): 6.89 (s,1), 2.68 (q,2, J = y7.2 Hz), 1.12 (6,3, J = 7.2 Hz).<br>Infrared (KBr): 3440, 2980, 2942, 1660, 1580, 1540, 1498, 1428, 1350, 1050, 854, 800, and 758 cm.$^{-1}$.<br>Anal. found: C, 35,63; H, 3.07; N, 9.12. |
| 45 (30) | 6-ACETYL-3,4-DIHYDRO-5-METHYL-4-OXOTHIENO[2,3-d]PYRIMIDINE-2-CARBOXYLIC ACID DISODIUM SALT SESQUIHYDRATE C$_{10}$H$_8$N$_2$O$_4$S . 2Na . 1½H$_2$O. - Yellow solid which fails to melt at 360° C.<br>NMR (CF$_3$COOH): 3.10 (s,3), 2.83 (s,3).<br>Infrared (KBr): 3460, 1665, 1633, 1580, 1484, 1438, 1370, 1350, 1305, 1259, 1060, and 812 cm.$^{-1}$.<br>Anal. found: C, 37.20; H, 2.65; N, 8.36. |
| 46 (58) | E-3-(3,4,5,6,7,8-HEXAHYDRO-4-OXOBENZOTHIENO[2,3-d]-PYRIMIDIN-2-YL)-2-PROPENOIC ACID DISODIUM SALT HYDRATE C$_{13}$H$_{10}$N$_2$O$_3$S . 2Na . 3 . 5H$_2$O. - Product precipitated by treatment of the reaction mixture with isopropanol; tan solid, failed to melt at 300° C.<br>NMR (DMSO-d$_6$): 6.98 (s,2), 2.80 (m,4), 1.75 (m,4).<br>Infrared (KBr): 3400, 2930, 2850, 1652, 1565, 1540, 1395, 1290, 1150, 968, and 806 cm.$^{-1}$.<br>Anal. found: C, 40.50; H, 4.10; N, 7.12. |
| 47 (51) | 5-AMINO-6-ETHYL-3,4-DIHYDRO-4-OXOTHIENO[2,3-d]PYRIMIDINE-2-CARBOXYLIC ACID DISODIUM SALT SESQUIHYDRATE C$_9$H$_7$N$_3$O$_3$S . 2Na . 1 . 5H$_2$O. - Methanol used as reaction medium; product precipitated with isopropanol; yellow powder, failed to melt at 250° C.<br>NMR (DMSO-d$_6$): 2.84 (q,2, J = 7.2 Hz), 1.25 (t,3, J = 7.2 Hz).<br>Infrared (KBr): 3405, 2975, 1655, 1625, 1590, 1538, 1505, 1410, 1360, 1295, 1050, 809, and 765 cm.$^{-1}$.<br>Anal. found: C, 35.34; H, 3.35; N. 13.20. |

Procedure 48. ETHYL 3,4-DIHYDRO-5-METHYL-6-NITRO-4-OXO-THIENO[2,3-d]PYRIMIDINE-2-CARBOXYLATE The product of Procedure 16, 1.0 g. is dissolved in 10 ml. of trifluoroacetic acid and 5 ml. of acetic anhydride is added to the mixture while it is cooled at $-15°$ C. A solution of 1.2 ml. of concentrated nitric acid in 4 ml. of trifluoroacetic acid is then added drop-wise to the solution with stirring at a temperature of $-12°$ to $-15°$ C. After a finely divided yellow precipitate forms, water, 100 ml., is added to the reaction mixture, and the precipitate is collected on a filter. This material is the desired product which is recrystallized from ethanol, m.p. $229°-229.5°$ C.

Anal. found: C, 42.23; H, 3.32; N, 14.84.

Procedure 49. ETHYL 6-AMINO-3,4-DIHYDRO-5-METHYL-4-OXO-THIENO[2,3-d]PYRIMIDINE-2-CARBOXYLATE The product of Procedure 48, 2.10 g. is dissolved in 100 ml. of dry dimethylformamide and hydrogenated at atmospheric pressure over 1 g. of a 10% dispersion of palladium carbon. Approximately 5 min. is required for absorption of the calculated quantity of hydrogen by the reaction solution. The catalyst is removed by filtration and the filtrate is poured into 1 l. of cold water. The product is recovered from the aqueous solution by extraction with chloroform, and the orange solid remaining on evaporation of the solvent is triturated with isopropanol, and recrystallized from methanol, yellow needles, m.p. $199.5°-215.0°$ C.

NMR (DMSO-$d_6$): 11.40 (bs.1), 6.20 (bs,2), 4.30 (q,2, J=7.0 Hz), 2.25 (s,3), and 1.30 (t,3, J=7.0 Hz). Infrared (KBr): 3422, 3315, 3190, 2996, 1728, 1645, 1622, 1552, 1450, 1365, 1335, 1280, 1180, 1032, 1010, and 770 cm.$^{-1}$.

Anal. found: C, 47,38; N. 4.33; N. 16.60.

Procedure 50. ETHYL 6-ETHYL-3,4-DIHYDRO-5-NITRO-4-OXO-THIENO[2,3-d]PYRIMIDINE-2-CARBOXYLATE The product of Procedure 29, 5 g., is converted to the desired product according to the method of Procedure 48. The product is a pale yellow solid which is recrystallized from a mixture of chloroform and ethanol, white crystals, m.p. $200.0°-212.0°$ C.

NMR (DMSO-$d_6$): 13.40 (bs,1), 4.45 (q,2, J=7.0 Hz), 3.02 (q.2, J=7.2 Hz), 1.39 (t,3, J=7.0 Hz), 1.31 (t,3, J=7.2 Hz). Infrared (KBr): 3190, 3115, 3060, 2995, 2950, 2900, 1755, 1665, 1550, 1525, 1492, 1373, 1315, 1298, 1192, and 795 cm.$^{-1}$.

Anal. found: C, 43.89; H, 3.67; N, 14.08.

Procedure 51. ETHYL 5-AMINO-6-ETHYL-3,4-DIHYDRO-4-OXO-THIENO[2,3-d]PYRIMIDINE-2-CARBOXYLATE The product of Procedure 50 is hydrogenated according to the method of Procedure 49. Approximately 3 hrs. is required for the calculated quantity of hydrogen to be absorbed. The catalyst is removed by filtration and the product recovered by concentration of the filtrate to dryness. The residue is recrystallized from a mixture of methanol and isopropanol to yield a yellow powder, m.p. $181.5°-184.5°$ C.

NMR (CDCL$_3$): 10.50 (bs,1), 4.60 (q,2, J=7.1 Hz), 4.09 (bs,2), 2.74 (q,2, J=7.2 Hz), 1.48 (t,3, J=7.1 Hz), 1.33 (t,3, J=7.2 Hz). Infrared (KBr): 3390, 3240, 2965, 2920, 1720, 1700, 1612, 1562, 1491, 1470, 1370, 1305, 1180, 795, and 785 cm.$^{-1}$.

Anal. found: C, 49.04; H, 4.88; N, 15.56.

Procedure 52. ETHYL 3,4-DIHYDRO-6-ETHYL-5-IODO-4-OXO-THIENO[2,3-d]PYRIMIDINE-2-CARBOXYLATE The product of Procedure 29, 2.65 g. (0.0105 mole), and 10.60 g. (0.034 mole) of mercuric acetate are dissolved in 35 ml. of glacial acetic acid and heated on a steam bath for 1 hr. The mixture is then poured into 400 ml. of saturated sodium chloride solution resulting in precipitation of the 5-chloromercuri intermediate, m.p. 237° C. (dec.). This intermediate, 4.10 g., is then added to a solution of 4 g. of iodine and 10 g. of potassium iodide in 150 ml. of water. The mixture is kept at room temperature with stirring for 3 days and then the purplish-black solid is collected on a filter and washed with ethanol to yield 2.70 g. of tan solid, fails to melt at 240° C. This material is recrystallized from methanol to give a pale yellow, crystalline product, m.p. $188.0°-190.0°$ C.

Anal. found: c, 35.15; H, 3.10; N, 7.36.

Procedure 53. 2-(HYDROXYMETHYL)-5-METHYL-6-(2-METHYLPROPYL)THIENO[2,3-d]PYRIMIDINE-4-(3H)-ONE.

The product of Procedure 28, 2.0 g. (0.0069 mole) is added in portions to a solution of 2.0 g. (0.052 mole) of sodium borohydryde in 150 ml. of absolute ethanol. Foaming occurs during the addition and the solution turns yellow in color. The mixture is kept at room temperature with stirring for 2 hrs. It was then poured into ice water with stirring and the mixture is acidified with glacial acetic acid. The acidified solution is then extracted with chloroform and the solvent evaporated from the extract to yield a yellow solid. On recrystallization from ethyl acetate, the product is obtained as a white crystalline solid, m.p. $182°-183°$ C.

NMR (CDCl$_3$): 4.69 (s,2), 2.56 (t,2, J=6.5 Hz), 2.47 (s,3), 1.80 (m,1), 0.95 (d,6, J=6.4 Hz). Infrared (KBr): 3320, 3100, 2960, 2875, 1670, 1592, 1381, 1315, 1210, 1090, and 1037 cm.$^{-1}$.

Anal. found: C, 57.31; H, 6.45; N, 11.08.

Procedure 54. 2-(HYDROXYMETHYL)-5-METHYL-6-PENTYL-THIENO[2,3-d]PYRIMIDINE-4(3H)-ONE.

This substance was prepared by the method of Procedure 53 employing as starting material the product of Procedure 17. Recrystallized from ethyl acetate, light yellow crystalline solid, m.p. $158.5°-159.5°$ C.

NMR (CDCl$_3$): 4.57 (s,2), 2.78 (t,2, J=7.0 Hz), 2.50 (s,3), 1.46 (m,6), 0.93 (m,3). Infrared (KBr): 3350, 2962, 2930, 2860, 1672, 1606, 1442, 1316, 1215, 1120, 1038, and 782 cm.$^{-1}$.

Anal. found: C, 58.83; H, 6.83; N, 20.46.

Procedure 55. 5,6,7,8-TETRAHYDRO-2-(HYDROXYMETHYL)-BENZOTHIENO[2,3-d]-4(3H)-PYRIMIDINONE.

The product of Procedure 2, 1.0 g., is suspended in 50 ml. of absolute ehtanol and 2.0 g. of lithium borohydryde is added portionwise thereto. Evolution of a gas occurs and the mixture is stirred at room temperature for 1½ hrs. and then refluxed for 20 min. The mixture is poured into 300 ml. of water, and the aqueous mixture is then acidified with glacial acetic acid. The desired product precipitates and is collected on a filter as fine yellow needles, recrystallized from a mixture of dimethylformamide and ethanol, m.p. 262.5°–268.5° C.

NMR (DMSO-$d_6$): 5.36 (bs,1), 4.35 (s,2), 2.76 (m,4), 1.77 (m,4). Infrared (KBr): 3120, 2940, 2860, 1670, 1590, 1450, 1350, 1300, 1200, 1153, 1080, 1040, 970, 905, and 795 cm.$^{-1}$.

Anal. found: C, 56.02; H, 5.09; N, 11.88.

Procedure 56:
6-HEXYL-2-(HYDROXYMETHYL)-5-METHYL-THIENO[2,3-d]PYRIMIDINE-4-(3H)-ONE.

The method of Procedure 53 is applied to the product of Procedure 15 for the production of this substance; recrystallized from ethyl acetate; light tan powder, m.p. 136.0°–140.0° C.

NMR (DMSO-$d_6$): 11.30 (bs,1), 5.22 (bs,1), 4.33 (s,2), 2.71 (t,2, J=6.6 Hz), 2.38 (s,3), 1.31 (m,8), 0.85 (m,3). Infrared (KBr): 3180, 1950, 2920, 2844, 1670, 1595, 1460, 1309, 1208, 1115, 1020, 770 cm.$^{-1}$.

Anal. found: C, 59.76; H, 6.98; N, 9.83.

Procedure 57.
(3,4,5,6,7,8-HEXAHYDRO-4-OXOBENZO-THIENO[2,3-d]PYRIMIDIN-2-YL)METHYL ACETATE.

The product of Procedure 55, 0.68 g., (0.00288 mole) is dissolved in 30 ml. of acetonitrile containing 5 ml. of acetic anhydryde and 5 ml. of pyridine, and heated for 30 min. at 100° C. The mixture is the poured into 150 ml. of cold water yielding the desired product as a pale yellow solid which is recrystallized from ethyl acetate; light yellow needles, m.p. 202.0°–204.0° C.

NMR (CDCl$_3$): 11.20 (bs,2), 5.08 (s,2), 2.90 (m,4), 2.20 (s,3), 1.86 (m,4). Infrared (KBr): 3125, 3020, 2950, 2900, 1760, 1673, 1612, 1281, 1260, 1239, 1050 cm.$^{-1}$.

Anal. found: C, 55.93; H, 5.12; N, 10.25.

Procedure 58. ETHYL 3-(3,4,5,6,7,8-HEXAHYDRO-4-OXOBENZO-THIENO[2,3-d]PYRIMIDIN-2-YL)-2-PROPENOATE.

A solution of sodium ethoxide in ethanol is prepared from 3.05 g. of sodium and 100 ml. of ethanol. A mixture of 24.5 g. (0.125 mole) of the product of Procedure 1 and 21.6 g. (0.125 mole) of diethyl fumarate in 300 ml. of ethanol is then added with the formation of a red solution which is stirred at the reflux temperature overnight. The mixture is then allowed to cool to room temperature and is poured into 1 l. of water containing 9 g. of acetic acid. The yellow precipitate forms during stirring for 1.5 hours at room temperature and it is collected by filtration; washed on the filter with water and dried, yellow solid, m.p. 285°–287° C.

NMR (CF$_3$COOH): 7.78 (d,1, J=16.1 Hz), 7.42 (d,1, J=16.1 Hz), 4.53 (q,2, J=7.2 Hz), 3.05 (m,4), 2.02 (m,4), 1.50 (t,3, J=7.2 Hz). Infrared (KBr): 3100, 2952, 1727, 1668, 1560, 1471, 1374, 1302, 1255, 1221, 1194, 1168, 990 and 970 cm.$^{-1}$.

Anal. found: C, 59.06; H, 5.25; N, 9.16.

Procedure 59. ETHYL (E)-3-(3,4,5,6,7,8-HEXAHYDRO-4-OXOBENZO-THIENO[2,3d][1,3]-OXAZIN-2-YL)-2-PROPENOATE.

To a suspension of 0.985 g. (0.005 mole) of 2-amino-4,5,6,7-tetrahydrobenzo[b]thiophene-3-carboxylic acid in 10 ml. of acetonitrile containing 1.2 ml. of pyridine which is cooled at 0° C., there is added with stirring 1.63 g. (0.010 mole) of ethyl fumaryl chloride. A clear solution forms on completion of the addition of the ethyl fumaryl chloride and the reaction mixture is stirred for an additional 1.5 hrs. at ice bath temperature. Stirring is continued overnight at room temperature and the precipitated solid is then collected by filtration and washed with ether, and finally with aqueous hydrochloric acid, aqueous potassium bicarbonate, and water. This material is purified by recrystallization from isopropanol and washed on the filter with isopropyl ether and low boiling petroleum ether; yellow crystaline solid, m.p. 147.5°–148.5° C.

NMR (CDCl$_3$): 7.16 (d,2, J=15.5 hz), 6.89 (d,1, J=15.5 Hz), 4.25 (q,2, J=7.1 Hz), 2.84 (m,4), 1.85 (m,4), 1.31 (t,3, J=7.1 Hz). Infrared (KBr): 2945, 2930, 2862, 1770, 1715, 1650, 1550, 1464, 1430, 1292, 1255, 1172, 974, and 768 cm.$^{-1}$.

Anal. found: C, 58.78; H, 4.97; N, 4.59.

Procedure 60.
6-ETHYL-2-(HYDROXYMETHYL)THIENO[2,3-d]PYRIMIDINE-4-(3H)-ONE.

The method of Procedure 53 is applied to the product of Procedure 29 to yield the desired product, recrystallized from 3:1 ethyl acetate:ethanol, m.p. 201.5°–202.5° C.

NMR (DMSO-$d_6$): 12.00 (bs,1), 7.12 (s,1), 5.64 (t,1, J=5.2 Hz), 4.47 (d,2, J=5.2 Hz), 2.90 (q,2, J=7.1 Hz), 1.30 (t,3, J=7.1 Hz). Infrared (KBr): 1083, 1140, 1153, 1200, 1279, 1300, 1366, 1428, 1461, 1485, 1535, 1567, 1584, 1640, 1675, 2829, 2844, 2871, 1938, and 2967 cm.$^{-1}$.

Anal. found: C, 51.19; H, 4.69; N, 13.25.

Procedure 61. ETHYL 6-HEXYL-4-OXO-4H-THIENO[2,3-d][1,3]OXAZINE-2-CARBOXYLATE.

This product is obtained by application of the method of Procedure 4 to 2-amino-5-(n-hexyl)thiophene-3-carboxylic acid. The ethyl oxalyl chloride is dissolved in acetonitrile prior to addition to the aminothiophene carboxylic acid which is dissolved in pyridine. The product is recovered as a light green solid which is recrystallized from ethanol, m.p. 80°–81° C.

NMR (CDCl$_3$): 7.30 (s,1), 4.58 (q,2, J=7.0 Hz), 2.93 (t,2, J=7.1 Hz), 1.48 (t,3, J=7.0 Hz), 1.40 (m,8), 0.92 (m,3). Infrared (KBr): 1285, 1308, 1366, 1388, 1436, 1436, 1462, 1478, 1541, 1586, 1715, 2829, 2861, and 2879 cm$^{-1}$.

Anal. found: C, 58.52; H, 6.16; N, 4.48.

Procedure 62. ETHYL 3,4-DIHYDRO-6-HEXYL-4-OXOTHIENO[2,3-d]PYRIMIDINE-2-CARBOXYLATE.

The product of Procedure 61 is treated with ammonium acetate and acetic acid in ethanol as described in Procedure 5 to yield this product, m.p. 114°–115° C.

NMR (CDCl$_3$): 11.00 (bs,1), 7.34 (s,1), 4.62 (q,2, J=7.0 Hz), 2.94 (t,2, J=7.2 Hz), 1.50 (t,3, J=7.0 Hz), 1.41 (m,8), 0.92 (m,3).

Infrared (KBr): 1035, 1104, 1149, 1195, 1221, 1241, 1313, 1373, 1401, 1415, 1481, 1569, 1689, 1741, 2834, 2865, and 2880 cm.$^{-1}$.

Anal. found: C, 58.49; H, 6.60; N, 9.29.

Procedure 63. ETHYL 6-CHLORO-3,4-DIHYDRO-5-METHYL-4-OXO-THIENO[2,3-d]PYRIMIDINE-2-CARBOXYLATE The product of Procedure 49, 0.01 mole, is dissolved in 20 ml. of 10% aqueous fluoboric acid and cooled to 0° C. A solution of sodium nitrite, 0.01 mole, in 5 ml. of water is added in drop-wise fashion. The mixture is stirred at 0° C. for 30 min. and then the bulky precipitate of 2-carbethoxy-3,4-dihydro-5-methyl-4-oxothieno[2,3-d]pyrimidin-6-yl diazonium fluoborate is collected on a filter and air dried. The latter, 0.01 mole, is then added in portion-wise fashion to a solution containing a stoichiometric excess of cuprous chloride in concentrated hydrochloric acid at 0° C. When all of the diazonium salt had been added, the temperature was allowed to warm to 20° C. and the mixture was then poured into ice water and the product filtered yielding the desired 6-chloro compound.

Procedure 64. ETHYL 6-ETHYL-3,4-DIHYDRO-5-HYDROXY-4-OXO-THIENO[2,3-d]PYRIMIDINE-2-CARBOXYLATE The diazonium fluoborate salt is prepared as in Procedure 63 from the amino compound produced in Procedure 51 yielding 0.03 mole of the required diazonium fluoborate. The latter is added in one portion to a solution of 0.03 mole of potassium trifluoroacetate in 13 ml. of trifluoroacetic acid at 0° C. The mixture is stirred at 25° C. for one hour and then refluxed overnight. The trifloroacetic acid is evaporated in vacuo to give a residue which is triturated with water and filtered to give the desired product.

Procedure 65. ETHYL 6-ETHYL-3,4-DIHYDRO-5-METHOXY-4-OXO-THIENO[2,3-d]PYRIMIDINE-2-CARBOXYLATE The product of Procedure 64, 0.01 mole is dissolved in 100 ml. of ether containing 1 chemical equivalent of boron trifluoride etherate relative thereto and the solution is cooled to 0° C. with stirring. A solution of 0.011 mole of diazomethane in 50 ml. of ether is then added portion-wise and the mixture is stirred at 0° C. until the yellow color disappears. Evaporation of the solvent yields the desired 5-methoxypyrimidine compound.

Procedure 66. 5,6,7,8-TETRAHYDRO-2-(5-TETRAZOLYL)BENZOTHIENO[2,3-d]PYRIMIDINE-4-(3H)-ONE The product of Procedure 2, 1.0 g. (0.0036 mole) is added to 30 ml. of concentrated aqueous ammonia. Sufficient ethanol is then added to form a clear solution and the mixture is clarified by filtration of a small amount of insoluble material. The solution is kept 4 hours at room temperature while a pale yellow precipitate forms. The latter is collected by filtration and air dried to yield 0.80 g. of 3,4,5,6,7,8-hexahydro-4-oxobenzothieno[2,3-d]pyrimidine-2-carboxamide, pale yellow solid, m.p. 278.0°–281.0° C. (dec.).

NMR (CDCl₃): 12.48 (s,1), 8.30 (s,1), 7.90 (s,1), 2.75 (m,4), 1.75 (m,4). Infrared (KBr): 1690 cm.$^{-1}$.

Anal. found: C, 53.12; H, 4.45; N, 16.93.

The latter, 0.01 mole, is then added to a mixture of 5 g. of phosphorous pentachloride in 10 ml. of phosphorous oxachloride. After the initial exothermic reaction subsides, the mixture is heated at 120° C. for 1 hour and then poured into ice water and the insoluble material collected on the filter. The collected material is air dried to yield 4-chloro-2-cyano-5,6,7,8-tetrahydro-4-oxobenzothieno[2,3-d]pyrimidine-4-(3H)-one. The latter is dissolved in 100 ml. of dimethylformamide containing 1.5 g. of sodium azide and 1.0 g. of ammonium chloride. The mixture is heated for 24 hours at 105°–110° C. The mixture is poured into ice water and the precipitated 4-azido-2-(5-tetrazolyl)-5,6,7,8-tetrahydrobenzothieno[2,3-]pyrimidine-4-(3H)-one is collected. The latter on hydrolysis with 2 chemical equivalents of sodium hydroxide dissolved in ethanol yields the desired product as the sodium salt.

procedure 67. 5,6,7,8-TETRAHYDRO-2-N-(TETRAZOL-5-YL)CARBAMYL BENZOTHIENO[2,3-d]PYRIMIDINE-4-(3H)-ONE The product of Procedure 32 is treated with 20 ml. of thionyl chloride at room temperature until gas evolution ceases. The excess thionyl chloride is then evaporated in vacuo and the residual acid chloride is dissolved in 25 ml. of dry dimethylformamide. 5-Aminotetrazole, 0.01 mole, is then added to the mixture which is stirred at room temperature for 1 hour and then heated on the steam bath for 2 hours. The mixture is then poured into water and filtered to yield the desired product.

Procedure 68. 3-BUTYL-3,4,5,6,7,8-HEXAHYDRO-4-OXOBENZOTHIENO[2,3-d]PYRIMIDINE-2-CARBOXYLIC ACID SODIUM SALT HEMIHYDRATE
$C_{15}H_{18}N_2O_3S \cdot Na \cdot \frac{1}{2}H_2O$ A mixture of 2.79 g. (0.01 mole) of the product of Procedure 20 and 0.73 g. (0.01 mole) of n-butylamine in 50 ml. of absolute ethanol is heated on a steam bath at reflux temperature for 4 hrs. The mixture is then poured into 500 ml. of cold water and extracted with chloroform. The extract is dried over magnesium sulfate and concentrated in vacuo to give 2.83 g. of a brown oil which crystalizes. The crystalline mass is tritrated with 1:1 ether-low boiling petroleum ether and the crystalline material is removed by filtration. The mother liquor is then concentrated in vacuo to a brown oil which is chromatographed on silica gel using 1:1 ether-low boiling petroleum ether for development to yield 1.52 g. of the desired product as the ethyl ester. The latter is saponified according to the method of Procedure 3 and the resulting sodium salt is recrystallized from isopropanol-ether to yield 0.90 g. (59%) of the desired product as an off-white powder, m.p. 265.0°–285.0° C. (dec.).

NMR (D₂O): 4.04 (m,2), 2.58 (m,4) 1.62 (m,8), 0.92 (m,3). Infrared (KBr): 2930, 2860, 2680, 2635, 1530, 1450, 1390, 1370, 1190, 1150, 1135, 905, 821, 780 and 744 cm.$^{-1}$.

Anal. found: C, 53.17; H, 5.31; N, 8.01.

Procedure 69. 6-ETHYL-3,4-DIHYDRO-3-METHYL-4-OXO-THIENO[2,3-d]PYRIMIDINE-2-CARBOXYLIC ACID SODIUM SALT The method of Procedure 68 is applied to the oxazine produced by Procedure 23 with substitution of methylamine fo the butylamine used in Procedure 68 to yield the desired product.

Procedure 70. ETHYL 3,4-DIHYDRO-6-FLUORO-5-METHYL-4-OXO-THIENO[2,3-d]PYRIMIDINE-2-CARBOXYLATE 2-Carbethoxy-3,4-dihydro-5-methyl-4-oxothieno[2,3-d]pyrimidin-6-yl diazonium fluoborate, 0.03 mole, is prepared as described in Procedure 63. The latter is then heated in an oil bath with adequate ventilation to carry off the boron trifluoride liberated by this treatment. A temperature of about 150° C. is sufficient and heating is continued until gas evolution is no longer evident. The residue is cooled, tritrated with water, and filtered to yield the desired compound.

Procedure 71. 3,4,5,6,7,8-HEXAHYDRO-4-OXOBENZO-THIENO[2,3-d]PYRIMIDINE-2-CARBOXALDEHYDE To a solution of 0.01 mole of the product of Procedure 55, and 0.3 mole of dicyclohexylcarbodiimide in 100 ml. of dimethyl sulfoxide there is added 0.01 mole of anhydrous orthophosphoric acid. The mixture is stirred at room temperature for 4 hrs. and 250 ml. of ethyl acetate is then added thereto followed by a solution of 25 g. of oxalic acid in methanol. Insoluble by product dicyclohexylurea is removed by filtration. The filtrate is washed with dilute aqueous sodium bicarbonate solution, the organic layer separated, and dried over magnesium sulfate. Evaporation of the solvent in vacuo, affords the desired product.

Procedure 72. ETHYL 5,6-DIHYDRO-4-OXO-4H-CYCLOPENTA[b]-THIENYL[2,3-d][1,3]OXAZINE-2-CARBOXYLATE Procedure 4 is adapted to the preparation of this product by using 2-amino-4,5-dihydrocyclopenta[b]thiophene-3-carboxylic acid as starting material.

Procedure 73. ETHYL 3,4,5,6-TETRAHYDRO-4-OXOCYCLOPENTA[b]-THIENO[2,3-d]PYRIMIDINE-2-CARBOXYLATE The oxazine produced in Procedure 72 is converted to this product by the method of Procedure 5.

Procedure 74. ETHYL 3,4,5,6-TETRAHYDRO-4-OXO-CYCLOPENTA[b]-THIENO[2,3-d][1,3]OXAZINE-2-CARBOXYLATE The method of Procedure 4 is adapted to the preparation of this substance by substitution of 2-amino-4,5,6,7-tetrahydrocyclohepta[b]thiophene-3-carboxylic acid as the starting material.

Procedure 75. ETHYL 3,4,5,6,7,8-HEXAHYDRO-4-OXOCYCLOHEPTA[b]-THIENO[2,3-d]PYRIMIDINE-2-CARBOXYLATE The product of Procedure 74 is converted to this substance by the method of Procedure 5.

Procedure 76. (3,4,5,6,7,8-HEXAHYDRO-4-OXOBENZO-THIENO[2,3-d]-PYRIMIDIN-2-YL)METHYLFORMATE The product of Procedure 55, 0.01 mole, is dissolved in a mixture of 30 ml. of acetic anhydride and 15 ml. of 100% formic acid at 0° C. The mixture is then allowed to warm to room temperature with stirring during a period of 1 hr. It is then poured into 200 ml. of ice water and the formate ester is collected.

Procedure 77. N-[3-(AMINOCARBONYL)-4,5,6,7-TETRAHYDROBENZO[b]THIEN-2-YL]OXAMIC ACID.

A suspension of 392 g. (2.0 mole) of 2-amino-4,5,6,7-tetrahydrobenzo[b]thiophene-3-carboxamide and 321.2 g. (2.2 mole) of diethyl oxylate in 5 l. of absolute ethanol is added to a solution of sodium ethoxide, prepared from 50.6 g. (2.2 g. atoms) of sodium, in 2 l. of absolute ethanol under nitrogen. The mixture is stirred with heating at the reflux temperature for 6 hrs. and then refrigerated overnight. It is then diluted with stirring to 15 l. with cool water. A finely divided precipitate forms which is removed by filtration. The filtrate is carefully acidified with 150 g. (2.5 mole) of acetic acid dissolved in 350 ml. of water. The resulting product which precipitates is collected on a filter, washed with water and air dried to yield 194.6 g. (0.7 mole) of the product of Procedure 2. The filtrate is acidified to pH 2 with concentrated hydrochloric acid and the resulting precipitate is collected on a filter, washed with water and air dried to give 264.8 g. (0.99 mole) of the desired product. A portion thereof weighing 25 g. is recrystallized from 1.4 l. of dioxane, yield 18.2 g., m.p. 223.5°–224.5° C. (dec.).

NMR (DMSO-$d_6$): 7.45 (s,2), 1.79 (s,8). Infrared (KBr): 3520, 3360, 3190, 2950, 2860, 1730, 1640, 1565, 1530, 1460, 1410, 1360, and 1290 cm.$^{-1}$.

Anal. found: C, 49.04; H, 4.47; N, 10.25.

Procedure 78. Tablets for Oral Ingestion.

The following ingredients are blended in the dry state in a twin-shell blender and compressed on a tablet press using an 11/32 inch die and concave punches.

| | |
|---|---|
| Product of Procedure 29 | 50.0 g. |
| Sucrose pregranulated for direct compression | 210.0 g. |
| Corn starch | 6.0 g. |
| Microcrystalline cellulose | 40.0 g. |
| Magnesium stearate | 1.0 g. |

This batch size is for 1,000 tablets and provides a tablet weighing 307 mg. supplying 50 mg. of active ingredient per tablet. Tablets containing from 25–200 mg. may be made employing the same ingredients, but adjusting the weight and tablet size appropriately.

Procedure 79. Solution for Injection.

The following ingredients are dissolved in sufficient water for injection to make 1.0 l. and the solution is filtered through a membrane filter having a pore size of 0.45 μm.

| | |
|---|---|
| Product of Procedure 44 | 0.2–5.0 g. |
| Sodium chloride to make isotonic | qs |
| Sodium phosphate buffered to pH | 7.5 |

The filtered solution is filled into clean sterile ampules and flame sealed followed by sterilization in an autoclave.

Procedure 80. Powder for Inhalation.

The following ingredients are blended aseptically and filled into hard gelatin capsules, each containing 50 mg. of the mixture providing 25 mg. of the active ingredient.

| Product of Procedure 36, micronized | 25.0 g. |
|---|---|
| Lactose powder | 25.0 g. |

The foregoing is sufficient for 1,000 capsules. These capsules are suitable for dispensing the powder into the inspired air stream using a breath actuated device. Appropriate adjustments of the composition can be made to give capsules containing 0.5–40 mg. of active ingredient.

Procedure 81.
3,4-DIHYDRO-6-HEXYL-4-OXOTHIENO[2,3-d]PYRIMIDINE-2-CARBOXYLIC ACID DISODIUM SALT HYDRATE
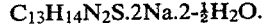

The method of Procedure 3 is applied to the product of Procedure 62. At the conclusion of the reaction period the product is precipitated by adding isopropanol to the reaction mixture. A white gelatinous precipitate forms and is collected on a filter and dried.

NMR (CF$_3$COOH): 7.52 (s,1), 3.10 (t,2, J=7.1 Hz), 1.52 (m,8), 0.93 (m,3). Infrared (KBr): 1265, 1346, 1375, 1429, 1471, 1495, 1579, 1605, 1660, 2828, 2861, and 2880 cm.$^{-1}$.

Anal. found: C, 42.34; H, 4.70; N, 7.42.

Procedure 82.
2-(HYDROXYMETHYL)-6-HEXYLTHIENO[2,3-d]PYRIMIDINE-4-(3H)-ONE.

The product of Procedure 62 is converted to this substance by the method of Procedure 53. The product is a tan solid.

NMR (CDCl$_3$): 11.60 (bs,1), 7.14 (s,1), 4.79 (s,2), 2.82 (t,2), 1.40 (m,8), 0.91 (m,3). Infrared (KBr): 1300, 1467, 1590, 1610, 1660, 2822, 2860, and 2878 cm.$^{-1}$.

The compound of Procedure 28, and the disodium salt of the corresponding carboxylic acid described in Procedure 43, are preferred species as inhibitors of the immediate hypersensitivity reaction. The corresponding dipotassium salt, which is described below in Procedure 97, is particularly preferred for inhibition of the immediate hypersensitivity reaction in mammals where allergic rhinitis is the manifestation. Due to its potency and water solubility the latter is suited for use as a nasal solution for application as drops, spray, or aerosol to the nasal mucosa. A powder composition for deposition on the nasal mucosa following insufflation similar to that of Procedure 80 except for micronization may be employed. For deposition on the nasal mucosa, a larger particle size of about 100μ is preferred. Systemic routes of administration including oral, rectal, buccal and parenteral may also be employed. The dipotassium salt (Procedure 97) exhibits the following ID$_{50}$ values in the PCA test described on pages 7-9 in rats: oral, 2.7 mg./kg.; intravenous, 0.14 mg./kg.

A publication describing work which is chemically related to the present disclosure is Arya, V.P., Indian Journal of Chemistry, 10, 1141–1150 (1972) which discloses the substance described above in Procedure 2.

The following procedures describe additional compounds and compositions falling within the scope of the invention.

Procedure 83. Ethyl N-[3-(Aminocarbonyl)thien-2-yl]oxamate.-

The method of Procedure 1 is applied to 2-aminothiophene-3-carboxamide to yield the desired product which is recrystallized from acetonitrile, m.p. 186.0°–187.0°.

Anal. Found: C, 44.52; H, 4.16; N, 11.56. NMR (DMSO-d$_6$): 1.34 (t, 3, 7.0 Hz), 4.48 (q, 2, 7.0 Hz), 7.26 (d, 1, 6.0 Hz), 7.65 (d, 1, 6.0 Hz), 7.80 (bs, 1), 8.19 (bs, 1), and 13.6 (bs, 1). IR: (KBr): 3415, 3390, 3180, 1730, 1685, 1650, 1590, 1550, and 1280 cm$^{-1}$.

This substance exhibits oral ED$_{50}$=4.5 mg./kg. of body weight in the rat PCA test for antiallergic activity described on pages 7–9 hereof.

Procedure 84. Ethyl 4-Oxo-6-pentyl-4H-thieno[2,3-d][1,3]oxazine-2-carboxylate.-

The method of procedure 4 is applied to 2-amino-5-pentylthiophene-3-carboxylic acid to yield the desired product as a crystalline solid; recrystallized from di-isopropyl ether, m.p. 69.6°–70.5°.

Anal. Found: C, 56.88; H, 5.62; N, 4.66. NMR (CDCl$_3$): 0.90 (t, 3, 6.0 Hz), 1.40 (m, 6), 1.47 (t, 3, 7.0 Hz), 2.93 (t, 2, 7.0 Hz), 4.58 (q, 2, 7.0 Hz), and 7.31 (s, 1). IR (KBr): 3100, 2960, 1770, 1590, 1470, 1430, 1320, 1130, 960, and 770 cm$^{-1}$.

Procedure 85. Ethyl 4-Oxo-6-propyl-4H-thieno[2,3-d][1,3-oxazine-2-carboxylate.-

The method of Procedure 4 is applied to 2-amino-5-propylthiophene-3-carboxylic acid. The resulting product is recrystallized from di-isopropyl ether, m.p. 90.5°–91.5° C.

Anal. Found: C, 53.61; H, 4.88; N, 5.22. NMR (CDCl$_3$): 1.03 (t, 3, 7.0 Hz), 1.50 (t, 3, 7.1 Hz), 1.87 (m, 2,), 2.92 (t, 2, 7.0 Hz), 4.60 (q, 2, 7.1 Hz), and 7.34 (s, 1). IR (KBr): 3120, 1800, 1750, 1375, 1330, 1170, 945, 840, and 765 cm$^{-1}$.

Procedure 86. Ethyl 6-Isopropyl-4-oxo-4H-thieno[2,3-d][1,3]-oxazine-2-carboxylate.-

The method of Procedure 4 is applied to 2-amino-5-isopropylthiophene-3-carboxylic acid for the production of the desired product which is recrystallized from di-isopropyl ether, m.p. 87.5°–88.5° C.

Anal. Found: C, 53.76; H, 4.79; N, 5.15. NMR (CDCl$_3$): 1.42 (d, 6, 6.5 Hz), 1.48 (t, 3, 6.6 Hz), 3.27 (septet, 1, 6.5 Hz), 4.57 (q, 2, 6.6 Hz), and 7.32 (s, 1). IR (KBr): 2980, 1780, 1740, 1585, 1475, 1430, 1315, 1205, 1160 and 760 cm$^{-1}$.

Procedure 87]. Ethyl 6-Butyl-4-oxo-4H-thieno[2,3-d][1,3]-oxazine-2-carboxylate.-

The method of Procedure 4 is applied to 2-amino-5-(n-butyl)thiophene-3-carboxylic acid. The resulting product is recrystallized from di-isopropyl ether, m.p. 76.0°–77.5° C.

Anal. Found: C, 55.42; H, 5.24; N, 4.93. NMR (CDCl$_3$): 0.96 (t, 3, 6.6 Hz), 1.50 (t, 3, 7.1 Hz), 1.60 (m, 4), 2.92 (t, 2, 7.2 Hz), 4.57 (q, 2, 7.1 Hz), and 7.33 (s, 1).

IR (KBr): 3100, 2980, 1770, 1590, 1430, 1370, 1320, 1130, 960, and 770 cm$^{-1}$.

Procedure 88. Butyl 6-Ethyl-3,4-dihydro-4-oxothieno[2,3-d]-pyrimidine-2-carboxylate.-

The product of procedure 29, 5.0 g. (0.019 mole) is dissolved in 20 ml. of butanol and 0.5 g. of p-toluenesulfonic acid is added thereto. The mixture is refluxed for 3 hrs., filtered while hot, and the product, which crystallizes on cooling, is collected and recrystallized from butanol, m.p. 116.0°–118.0° C.

Anal. Found: C, 56.06; H, 5.73; N, 10.14. NMR (CDCl$_3$): 1.03 (t, 3, 6.3 Hz), 1.42 (t, 3, 7.0 Hz), 1.81 (m, 4), 3.02 (q, 2, 7.0 Hz), 4.61 (t, 2, 6.0 Hz), 7.50 (s, 1), and 11.6 (bs, 1). IR (KBr): 3100, 2970, 1745, 1680, 1660, 1480, 1290, 1185, 840 and 770 cm$^{-1}$.

Procedure 89. Ethyl 3,4-Dihydro-4-oxothieno[2,3-d]pyrimidine-2-carboxylate.-

The product of Procedure 83 is converted to this substance by adaptation of the method of Procedure 2. The product is purified by cromatography on silica gel using chloroform for elution, and recrystallized from isopropanol, m.p. 191.0°–192.0° C.

Anal. Found: C, 47.78; H, 3.80; N, 12.19. NMR (CDCl$_3$): 1.50 (t, 3, 7.0 Hz), 4.66 (q, 2, 7.0 Hz), 7.60 (d, 1, 6.0 Hz), 7.76 (d, 1, 6.0 Hz), and 10.8 (bs, 1). IR (KBr): 3080, 1745, 1680, 1580, 1480, 1460, 1380, 1310, 1190 and 1040 cm$^{-1}$.

Procedure 90. Ethyl 6-Ethyl-3,4-dihydro-3-methyl-4-oxothieno-[2,3-d]pyrimidine-2-carboxylate.-

The method of Procedure 69 is repeated except that the saponification step following chromatography is omitted and two molecular equivalents of acetic acid relative to the oxazine starting material produced in Procedure 23 is included in the reaction mixture, The desired product is obtained as a dark oil.

Anal. Found: C, 53.86; H, 5.65; N, 9.58. NMR (CDCl$_3$): 1.36 (t, 3, 7.0 Hz), 1.49 (t, 3, 7.0 Hz), 2.91 (q, 2, 7.0 Hz), 3.72 (s, 3), 4.56 (q, 2, 7.0 Hz), and 7.31 (s, 1). IR (KBr): 2970, 1735, 1690, 1560, 1535, 1370, 1290, 1240, 1105 and 1020 cm$^{-1}$.

Procedure 91. Ethyl 3,4-Dihydro-6-methyl-4-oxothieno[2,3-d]pyrimidine 2-carboxylate.-

The method of Procedure 5 is applied to ethyl 6-methyl-4-oxo-4H-thieno[2,3-d][1,3]oxazine-2-carboxylate employing ethyl acetate as solvent. The product is recovered as a crystalline solid which may be recrystallized from 95% ethanol, m.p. 204.0°–208.0° C.

Anal. Found: C, 50.13; H, 4.13; N, 11.69. NMR (DMSO-d$_6$): 1.36 (t, 3, 7.0 Hz), 2.55 (s, 3), 4.36 (q, 2, 7.0 Hz), 7.26 (s, 1), and 13.0 (bs, 1). IR (KBr): 3280, 3000, 1750, 1710, 1480, 1310, 1285, 1180, 1025, 845, and 760 cm$^{-1}$.

Procedure 92. Ethyl 3,4-Dihydro-6-(1-methylethyl)-4-oxothieno[2,3-d]pyrimidine-2-carboxylate.-

The product of Procedure 86 is converted to the desired product by refluxing with ethanolic ammonium acetate and acetic acid according to the method of Procedure 5. The product is recrystallized from ethanol, m.p. 182°–183° C.

Anal. Found: C, 54.01; H, 5.19; N, 10.42. NMR (CDCl$_3$): 1.40 (d, 6, 6.5 Hz), 1.51 (t, 3, 7.0 Hz), 3.21 (septet, 1, 6.5 Hz), 4.52 (q, 2, 7.0 Hz), 7.33 (s, 1), and 10.6 (bs, 1). IR (KBr): 3100, 2960, 1740, 1690, 1570, 1480, 1300, 1185, 1050, and 765 cm$^{-1}$.

Procedure 93. 3,4-Dihydro-6-(1-methylethyl)-4-oxothieno[2,3-d]pyrimidine-2-carboxylic Acid Disodium Salt.-

The product of Procedure 92 is hydrolyzed with ethanolic sodium hydroxide according to the method of Procedure 3. The cooled reaction mixture is diluted with isopropanol and the product collected on a filter. It is air dried and ground in a mortar. It fails to melt when heated in a capillary tube at 350° C. The elemental analysis corresponded to the hydrate containing 1.75 moles of water per mole of the disodium salt.

Anal. Found: C, 38.28; H, 3.74; N, 8.56. NMR (D$_2$O): 1.15 (d, 6, 6.5 Hz), 2.90 (m, 1), 7.20 (s, 1) and 4.80. IR (KBr): 2860, 1650, 1570, 1425, 1365, 1340, 1060, 840 and 790 cm$^{-1}$.

Procedure 94. Ethyl 6-Butyl-3,4-dihydro-4-oxothieno[2,3-d]pyrimidine-2-carboxylate.-

The product of Procedure 87 is treated with ethanolic ammonium acetate containing acetic acid according to the method of Procedure 5. The product is recrystallized from ethanol-isopropanol, m.p. 144°–145° C.

Anal. Found: C, 55.58; H, 6.02; N, 10.00. NMR (CDCl$_3$): 0.98 (t, 3, 6.0 Hz), 1.52 (t, 3, 7.0 Hz), 1.53 (m, 4), 2.90 (t, 2, 7.0 Hz), 4.70 (q, 2, 7.0 Hz), 7.40 (s, 1), 11.3 (bs, 1), IR (KBr): 3110, 2960, 1740, 1670, 1490, 1300, 1180, 1030 and 770 cm$^{-1}$.

Procedure 95. Ethyl 3,4-Dihydro-4-oxo-6-propylthieno[2,3-d]pyrimidine-2-carboxylate.

The product of Procedure 85 is converted to the desired product by treatment with ethanolic ammonium acetate according to the method of Procedure 5 except that acetic acid is omitted. The product is recrystallized from ethanol, m.p. 169°–170° C.

Anal. Found: C, 54.49; H, 5.29; N, 10.53. NMR (CDCl$_3$): 1.03 (t, 3, 6.5 Hz), 1.52 (t, 3, 7.0 Hz), 1.88 (m, 2), 2.90 (t, 2, 6.7 Hz), 4.60 (q, 2, 7.0 Hz), 7.35 (s, 1), and 11.5 (bs, 1). IR (KBr): 3100, 2960, 1735, 1690, 1570, 1480, 1305, 1185, 1035, and 765 cm$^{-1}$.

Procedure 96. Ethyl 3,4-Dihydro-4-oxo-6-pentylthieno[2,3-d]pyrimidine-2-carboxylate.-

The oxazine produced in Procedure 84 is converted to this product by treatment with ethanolic ammonium acetate containing acetic acid according to the method of Procedure 5. The product is recrystallized from a mixture of ethanol and isopropanol, m.p. 124°–125° C.

Anal. Found: C, 57.22; H, 6.20; N, 9.52. NMR (CDCl$_3$): 0.87 (t, 3, 6.0 Hz), 1.40 (m, 6), 1.47 (t, 3, 7.0 Hz), 2.88 (t, 2, 7.0 Hz), 4.56 (q, 2, 7.0 Hz), 7.32 (s, 1) and 11.7 (bs, 1). IR (KBr): 3100, 2960, 1760, 1740, 1690, 1490, 1300, 1190, 1040 and 770 cm$^{-1}$.

Procedure 97.
3,4-Dihydro-5-methyl-6-(2-methylpropyl)-4-oxo-thieno[2,3-d]pyrimidine-2-carboxylic Acid Dipotassium Salt.-

The product of Procedure 28 is hydrolyzed by treatment of 1.91 g. thereof with 0.86 g. of potassium hydroxide dissolved in 150 ml. of isopropanol. The mixture is heated at reflux with stirring for 4 hrs. It is then allowed to cool and the product collected on a filter. It is ground in a morter and air dried. It failed to melt when heated in a capillary tube to 350° C. The elemental analysis indicated that the product was obtained as the hydrate containing 1.75 moles of water per mole of salt.

Anal. Found: C, 38.66; H, 4.25; N, 7.20. NMR ($D_2O$): 0.88 (d, 6, 6.0 Hz), 1.89 (m, 1), 2.40 (s, 3), 2.61 (d, 2, 6.5 Hz), and 4.80. IR (KBr): 2840, 1650, 1590, 1560, 1535, 1470, 1415, 1340, 1040, and 800 $cm^{-1}$.

Procedure 98.
3,4-Dihydro-3,5-dimethyl-6-octyl-4-oxothieno[2,3-d]pyrimidine-2-carboxylic Acid Sodium Salt.-

A mixture of 2.34 g. (0.0064 mole) of the oxazine produced in Procedure 4, 4.47 g. of 40% aqueous methylamine (0.0576 mole), and 5.00 g. (0.0832 mole) of glacial acetic acid is heated in 40 ml. of absolute ethanol on a steam bath for 40 min. The mixture is then worked up substantially as described in Procedure 5 to yield the desired product which melted at 310.0°–315.5° C. (dec.). The material is obtained as the hydrate containing 0.25 moles of water per mole of the salt.

Anal. Found: C, 56.36; H, 6.55; N, 7.70. NMR (DMSO-$d_6$): 0.84 (m, 3), 1.30 (m, 12), 2.41 (s, 3), 2.77 (m, 2), and 3.45 (s, 3). IR (KBr): 3480, 2940, 2870, 1665, 1650, 1550, 1380, 1330, 1130, 795 and 755 $cm^{-1}$.

Procedure 99.
6-Hexyl-2-(hydroxymethyl)thieno[2,3-d]pyrimidine-4-(3H)-one.-

The product of Procedure 62 is reduced with sodium borohydride according to the method of Procedure 53. The product is recrystallized from ethyl acetate, m.p. 141°–143° C.

Anal. Found: C, 58.84; H, 6.94; N, 10.13. NMR (CDCl$_3$): 0.90 (t, 3, 6.0 Hz), 1.35 (m, 9), 2.81 (t, 2, 7.0 Hz), 4.80 (s, 2), 7.12 (s, 1), and 11.6 (bs, 1). IR (KBr): 3270, 2930, 2860, 1665, 1610, 1600, 1470, 1300, 840 and 755 $cm^{-1}$.

Procedure 100. Solution For Nasal Application.-

A 1% solution of the product of Procedure 97 is prepared by dissolving it in an appropriate quantity of water with an effective amount of pharmaceutically acceptable microbial preventative, and sufficient sodium chloride to provide an isotonic solution. The pH is adjusted to pH 9.0 with hydrochloric acid and the product is packaged in bottles with dropper or spray attachment for nasal application.

What is claimed is:
1. The compound having Formula V

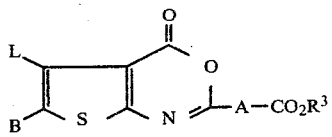

Formula V wherein
$R^3$ is selected from the group consisting of hydrogen, lower alkyl having 1 to 8 carbon atoms, and M wherein M is a non-toxic pharmacologically inert metal cation, and A is a covalent bond or it is —CH=CH—, L and B are independently selected from the group consisting of hydrogen, lower alkyl having 1 to 8 carbon atoms, lower alkenyl having 3 to 6 carbon atoms, phenyl, and alkanoyl having 2 to 6 carbon atoms, or together they constitute cycloalkene having 5 to 7 carbon atoms, or R-substituted cycloalkene having 5 to 7 carbon atoms wherein R is lower alkyl having 1 to 8 carbon atoms.

2. The compound of claim 1, wherein A is a co-valent bond.

3. The compound of claim 2, wherein L and B are lower alkyl.

4. The compound of claim 2, wherein one of L and B is hydrogen and the other is lower alkyl.

5. The compound of claim 2 wherein L and B are lower alkenyl.

6. The compound of claim 2 wherein one of L and B is hydrogen and the other is lower alkenyl.

7. The compound of claim 2 wherein one of L and B is lower alkyl and the other is lower alkenyl.

8. The compound of claim 1, ethyl 5,6,7,8-tetrahydro-4-oxo-4H-benzothieno[2,3-d][1,3]oxazine-2-carboxylate.

9. The compound of claim 1, ethyl 6-ethyl-5-methyl-4-oxo-4H-thieno[2,3-d][1,3]oxazine-2-carboxylate.

10. The compound of claim 1, ethyl 5-methyl-6-(2-methylpropyl)-4-oxo-4H-thieno[2,3-d][1,3]oxazine-2-carboxylate.

11. The compound of claim 1, ethyl 6-ethyl-4-oxo-4H-thieno[2,3-d][1,3]oxazine-2-carboxylate.

12. The compound of claim 1, ethyl 6-acetyl-5-methyl-4-oxo-4H-thieno[2,3-d][1,3]oxazine-2-carboxylate.

13. The compound of claim 1, ethyl 3,4-dihydro-5,6-dimethyl-4-oxothieno[2,3-d][1,3]oxazine-2-carboxylate.

14. The compound of claim 1, ethyl 6-hexyl-5-methyl-4-oxo-4H-thieno[2,3-d][1,3]-oxazine-2-carboxylate.

15. The compound of claim 1, ethyl (E)-3-(3,4,5,6,7,8-hexahydro-4-oxobenzothieno[2,3-d][1,3]oxazin-2-yl)-2-propenoate.

16. The compound of claim 1, ethyl 6-hexyl-4-oxo-4H-thieno[2,3-d][1,3]oxazine-2-carboxylate.

17. The compound of claim 1, ethyl 6-butyl-4-oxo-4H-thieno[2,3-d][1,3]oxazine-2-carboxylate.

18. The compound of claim 1, ethyl 4-oxo-6-pentyl-4H-thieno[2,3-d][1,3]oxazine-2-carboxylate.

19. The compound of claim 1, ethyl 4-oxo-6-propyl-4H-thieno[2,3-d][1,3]oxazine-2-carboxylate.

20. The compound of claim 1, ethyl 6-isopropyl-4-oxo-4H-thieno[2,3-d][1,3]oxazine-2-carboxylate.

21. The compound of claim 1, ethyl 5-methyl-6-octyl-4-oxo-4H-thieno[2,3-d][1,3]oxazine-2-carbohydrate.

22. A method of inhibiting the immediate hypersensitivity reaction in a sensitive mammal which comprises administering to said mammal an effective hypersensitivity reaction inhibiting dose of a compound selected from the group consisting of substances having Formula V

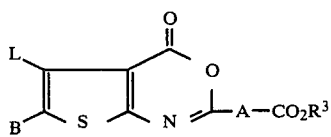

Formula V wherein
R³ is selected from the group consisting of hydrogen, lower alkyl having 1 to 8 carbon atoms, and M wherein M is a non-toxic pharmacologically inert metal cation, A is a covalent bond or it is —CH=CH—, and L and B are independently selected from the group consisting of hydrogen, lower alkyl having 1 to 8 carbon atoms, lower alkenyl having 3 to 6 carbon atoms, phenyl, and alkanoyl having 2 to 6 carbon atoms, or together they constitute cycloalkene having 5 to 7 carbon atoms, or R-substituted cycloalkene having 5 to 7 carbon atoms wherein R is lower alkyl having 1 to 8 carbon atoms.

23. The method of claim 22 wherein said immediate hypersensitivity reaction is an asthmatic attack.

24. The method of claim 22 wherein said immediate hypersensitivity reaction is allergic rhinitis.

25. The method of claim 22 wherein said immediate hypersensitivity reaction is urticaria.

26. A pharmaceutical composition in dosage unit form comprising a pharmaceutical carrier and an effective mammalian immediate hypersensitivity reaction inhibiting dose of a compound selected from the group consisting of Formula V,

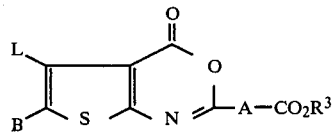

Formula V wherein
R³ is selected from the group consisting of hydrogen, lower alkyl having 1 to 8 carbon atoms, and M wherein M is a non-toxic pharmacologically inert metal cation, A is a covalent bond or it is —CH=CH—, L and B are independently selected from the group consisting of hydrogen, lower alkyl having 1 to 8 carbon atoms, lower alkenyl having 3 to 5 carbon atoms, phenyl, and alkanoyl having 2 to 6 carbon atoms, or together they constitute cycloalkene having 5 to 7 carbon atoms, or R-substituted cycloalkene having 5 to 7 carbon atoms wherein R is lower alkyl having 1 to 8 carbon atoms.

* * * * *